United States Patent
Lynch

(10) Patent No.: US 12,005,153 B2
(45) Date of Patent: *Jun. 11, 2024

(54) COMPOSITIONS AND METHODS FOR TREATING WOUNDS

(71) Applicant: Samuel Lynch, Franklin, TN (US)

(72) Inventor: Samuel E. Lynch, Franklin, TN (US)

(73) Assignee: Samuel E. Lynch, Franklin, TN (US)

( * ) Notice: Subject to any disclaimer, the term of this patent is extended or adjusted under 35 U.S.C. 154(b) by 281 days.

This patent is subject to a terminal disclaimer.

(21) Appl. No.: 16/663,337

(22) Filed: Oct. 25, 2019

(65) Prior Publication Data

US 2020/0164101 A1 May 28, 2020

Related U.S. Application Data

(63) Continuation-in-part of application No. 16/045,520, filed on Jul. 25, 2018, now abandoned, which is a continuation of application No. 15/256,339, filed on Sep. 2, 2016, now Pat. No. 10,071,182, which is a continuation of application No. PCT/US2015/055522, filed on Oct. 14, 2015, application No. 16/663,337 is a continuation-in-part of application No. 15/256,362, filed on Sep. 2, 2016, now abandoned, which is a continuation of application No. PCT/US2015/055522, filed on Oct. 14, 2015.

(60) Provisional application No. 62/063,793, filed on Oct. 14, 2014.

(51) Int. Cl.
| | |
|---|---|
| A61K 38/18 | (2006.01) |
| A61K 9/00 | (2006.01) |
| A61K 9/70 | (2006.01) |
| A61K 47/34 | (2017.01) |
| A61K 47/42 | (2017.01) |
| A61L 26/00 | (2006.01) |
| A61P 17/02 | (2006.01) |

(52) U.S. Cl.
CPC ........ *A61L 26/0066* (2013.01); *A61K 9/0014* (2013.01); *A61K 9/0024* (2013.01); *A61K 9/7007* (2013.01); *A61K 38/1858* (2013.01); *A61K 47/34* (2013.01); *A61K 47/42* (2013.01); *A61L 26/0023* (2013.01); *A61L 26/0033* (2013.01); *A61L 26/0052* (2013.01); *A61L 26/0085* (2013.01); *A61L 26/0095* (2013.01); *A61P 17/02* (2018.01); *A61L 2300/414* (2013.01); *Y02A 50/30* (2018.01)

(58) Field of Classification Search
CPC .............. A61K 38/1858; A61K 9/0014; A61K 9/7007; A61L 26/0033; A61L 26/0023; A61L 26/0085; A61L 26/0095; A61P 17/02

See application file for complete search history.

(56) References Cited

U.S. PATENT DOCUMENTS

2009/0036413 A1* 2/2009 McAnalley .............. A61K 9/06
514/163

FOREIGN PATENT DOCUMENTS

WO    WO 2009/146456    * 12/2009

OTHER PUBLICATIONS

Ramanujam et al. Foot Ankle Specialist, 2010, vol. 3(5):231-240.*

* cited by examiner

*Primary Examiner* — Xiaozhen Xie

(74) *Attorney, Agent, or Firm* — Epstein Becker Green

(57) ABSTRACT

An improvement to the effectiveness or "take" of skin grafts or tissue replacements used to treat wounds is provided. A therapeutic composition comprising recombinant human platelet-derived growth factor BB homodimer (rhPDGF-BB) and a porous biocompatible carrier is first applied to the wound surface, followed by applying a skin substitute or tissue replacements composition.

38 Claims, No Drawings

Specification includes a Sequence Listing.

```
SEQUENCE LISTING

<160> NUMBER OF SEQ ID NOS: 1

<210> SEQ ID NO 1
<211> LENGTH: 109
<212> TYPE: PRT
<213> ORGANISM: Artificial Sequence
<220> FEATURE:
<223> OTHER INFORMATION: Synthetic Construct

<400> SEQUENCE: 1

Ser Leu Gly Ser Leu Thr Ile Ala Glu Pro Ala Met Ile Ala Glu Cys
1               5                   10                  15

Lys Thr Arg Thr Glu Val Phe Glu Ile Ser Arg Arg Leu Ile Asp Arg
            20                  25                  30

Thr Asn Ala Asn Phe Leu Val Trp Pro Pro Cys Val Glu Val Gln Arg
        35                  40                  45

Cys Ser Gly Cys Cys Asn Asn Arg Asn Val Gln Cys Arg Pro Thr Gln
    50                  55                  60

Val Gln Leu Arg Pro Val Gln Val Arg Lys Ile Glu Ile Val Arg Lys
65                  70                  75                  80

Lys Pro Ile Phe Lys Lys Ala Thr Val Thr Leu Glu Asp His Leu Ala
                85                  90                  95

Cys Lys Cys Glu Thr Val Ala Ala Ala Arg Pro Val Thr
            100                 105
```

COMPOSITIONS AND METHODS FOR TREATING WOUNDS

CROSS REFERENCE TO RELATED APPLICATIONS

The present application is a continuation-in-part of U.S. patent application Ser. No. 16/045,520, filed Jul. 25, 2018, now abandoned, which is a continuation of U.S. patent application Ser. No. 15/256,339, filed Sep. 2, 2016, now U.S. Pat. No. 10,071,182, which is a continuation of PCT International Application Serial No. PCT/US2015/055522, filed Oct. 14, 2015, which claims the benefit of U.S. Provisional Patent Application No. 62/063,793 filed on Oct. 14, 2014, and a continuation-in-part of U.S. patent application Ser. No. 15/256,362, filed Sep. 2, 2016, now abandoned, which is a continuation of PCT International Application Serial No. PCT/US2015/055522, filed Oct. 14, 2015, which claims the benefit of U.S. Provisional Patent Application No. 62/063,793 filed on Oct. 14, 2014, the entire contents of which applications are incorporated herein by reference.

SEQUENCE LISTING

The instant application contains a Sequence Listing which has been submitted in ASCII format via EFS-Web and is hereby incorporated by reference in its entirety. The ASCII copy, created on Feb. 5, 2020, is named 20200205Sequence-Listing.txt and is 2.0 Kilobytes in size.

TECHNICAL FIELD

The present invention relates to compositions and methods useful for improved treatment of a skin wound by one or more treatments with a therapeutic composition comprising rhPDGFBB and a skin-substitute composition.

BACKGROUND

Healing of Wounds

Cutaneous wound repair normally consists of a complex, interdependent cascade of events including inflammation, angiogenesis, proliferation of connective tissue cells, collagen and extracellular matrix synthesis, subsidence of inflammation, epithelial cell transmembrane changes, mobilization and reepithelialization of the wounded area, and finally remodeling of the scar at the healed site. Each of these steps in the healing cascade is itself highly complex and governed by numerous cellular and molecular regulatory pathways. During normal healing these events occur in a well-organized sequence, whereas during delayed healing or non-healing situations the sequence may stop at any step along the healing progression. Delayed healing has a number of etiologies, such as the taking of certain drugs (e.g., steroids), metabolic disorders (e.g., diabetes), smoking, age related changes, blood pressure, arteriole and venous insufficiencies, and neurological impairment. These pathologies may result in delay or disorganization of any one of the steps in healing, leading to a failure of the wound to progress through the highly orchestrated healing process. Delayed healing of wounds can result in numerous complications, such as infection, bacteremias, systemic sepsis and local tissue necrosis possibly leading to amputations and limb loss.

It is estimated that 6 million patients in the United States have chronic, non-healing wounds and 35 million patients require acute wound care annually. At present, chronic wounds are refractory to current standard therapy and represent a major health care problem, especially for the increasing elderly population. The rapid growth in the prevalence of diabetes—an astounding 380 million people worldwide—is also contributing to growth in the prevalence of poorly healing wounds. The estimated incidence of diabetes in the US exceeds 1.9 million new cases annually, with an overall prevalence of 25.8 million people or 8.3% of the nation's population. If current trends continue, it is estimated that 1 in 3 adult Americans will have diabetes by 2050. A higher incidence of diabetes occurs among non-Hispanic blacks, Hispanic/Latino Americans, and Native Americans compared with non-Hispanic whites.

Patients with diabetes are at risk for developing serious health problems that may affect the feet, eyes, kidneys, skin and heart. Foot ulcerations are one of the most common and serious complications in patients with diabetes. Up to 25% of diabetics can expect to develop a foot ulcer at some point in their lifetime. The prevalence of DFUs among diabetics is 4% to 10%. More than half of all foot ulcers will become infected requiring hospitalization, and 1 in 5 will require amputation. Foot ulcers account for 85,000 non-trauma related lower limb amputations annually. It is estimated that every 20 seconds, somewhere in the world, a limb is lost as a consequence of diabetic wounds. Moreover, 85% of leg amputations are preceded by DFUs, and more than 60% of non-traumatic lower extremity amputations (LEA) performed in the United States each year occur secondary to complications of diabetes mellitus. After a major amputation, 50% of patients will have another limb amputated within two years. Mortality rates subsequent to amputation are alarmingly high and reach up to 40% at 1 year and 800% at 5 years. Patients with a history of a diabetic foot ulcer have a 40% greater mortality rate compared to patients with diabetes alone.

Clearly failure of wounds to respond to the best currently available therapies is a major health care problem worldwide. New effective treatments are desperately needed to address this large and growing health care problem.

Skin Substitutes

Skin loss can occur for many reasons, including acute trauma, chronic wounds, genetic disorders (bullous conditions), or surgical interventions. Acute thermal trauma is one of the most common reasons for major skin loss. Burns can result in extensive wounds that cannot be successfully treated with common techniques. Skin substitutes, such as autologous skin grafts, are commonly used to treat skin wounds resulting from thermal trauma, chronic wounds, etc., which are 1 cm or more in diameter.

Chronic wounds, those wounds that generally do not heal within about three months, are another common reason for skin loss. When the normal repair response goes awry, there are two major outcomes: either an ulcerative skin defect (chronic or non-healing wound) or an excessive formation of scar (hypertrophic scar or keloid). Poor wound healing after trauma, surgery, acute illness, or chronic disease conditions affects millions of people worldwide each year and is the consequence of dysregulated elements of the healthy tissue repair response, including inflammation, angiogenesis, matrix deposition, and cell recruitment. Failure of one or several of these cellular processes is generally linked to an underlying clinical condition, such as vascular disease, diabetes, or aging, which are all frequently associated with healing pathologies.

The current standard for skin substitutes is the autologous split-thickness skin graft (STSG). Epidermis with a superficial part of the dermis is harvested from an undamaged skin donor site and applied to the wound. The split-thickness skin graft must connect indirectly or directly with the existing blood supply or capillary network in or around the wound bed to provide oxygen and nutrients for graft cell survival. This connection is referred to as graft "take." Full-thickness skin grafts (FTSGs), on the other hand, consist of the entire epidermis and dermis with preservation of deep dermal elements that allow better recovery of the normal physiological functions of the grafted skin with far less scarring. The thicker FTSG, however, have greater metabolic needs and a higher incidence of graft failure than the STSG. Unreliable graft take remains a problem even with STSGs. (See C. L. Rettinger, J. L. Fletcher, A. H. Carisson, R. K. Chan, "Accelerated epithelialization and improved wound healing metrics in porcine full-thickness wounds transplanted with full-thickness skin micrografts," *Wound Rep. Reg.* 25:816-827 (2017); reviewed in R. V. Shevchenko, S. L. James, and S. E. James, "A Review of Tissue-Engineered Skin Bioconstructs Available for Skin Reconstruction," *J. R. Soc. Interface.* 7(43): 229-258 (2010); published online 2009 Oct. 28. doi: 10.1098/rsif.2009.0403.)

Another approach is cell-based strategy, involving the development of skin substitutes using cultured human epidermal keratinocytes and other dermal substitutes that have qualities similar to native skin. Several companies have manufactured "living skin equivalents" of autologous and allogeneic primary cells harvested from explant material. During the last two decades, many of these products have received FDA approval for the treatment of large and diseased skin defects that are refractory to conventional therapy. (Reviewed in Shevchenko et al., 2010.) Clinically effective, FDA-approved treatments for DFUs, for example, include skin substitutes using fibroblasts delivered in an absorbable mesh (W. A. Marston, J. Hanft, P. Norwood, and R. Pollak, "The efficacy and safety of Dermagraft in improving the healing of chronic diabetic foot ulcers: results of a prospective randomized trial," *Diabetes Care.* 26:1701-1705 (2003)), and fibroblasts and keratinocytes delivered in type 1 collagen (H. Brem, J. Balledux, T. Bloom, M. D. Kerstein, and L. Hollier, "Healing of diabetic foot ulcers and pressure ulcers with human skin equivalent: a new paradigm in wound healing," *Arch. Surg.* 135:627-634 (2000)).

Despite the development of new therapies, the effectiveness of skin grafting and tissue replacement to treat diabetic foot ulcers has been modest at best. An analysis of 17 clinical studies involving treating foot ulcers with skin grafts or tissue replacements as compared to standard care, and which totaled 1655 patients, concluded that although there was an increase in the healing rate, the skin graft and tissue replacement treatments lead to only slightly fewer amputations. The analysis also concluded that evidence of long term effectiveness is lacking, and cost-effectiveness is uncertain. (T. B. Santema, P. P. C. Poyck, D. T. Ubbink, "Skin grafting and tissue replacement for treating foot ulcers in people with diabetes," *Cochrane Database of Systematic Reviews Issue* 2 (2016) Art. No.: CD011255. DOI: 10.1002/14651858.CD011255.pub2.

Growth Factor Therapies

The molecular mechanisms of wound healing are complex. Over 100 physiologic factors were known by 2007 to contribute to wound healing deficiencies in individuals with diabetes, for example. (Reviewed in H. Brem and M. Tomic-Canic, "Cellular and molecular basis of wound healing in diabetes," *J. Cli. Invest.* 117(5): 1219-1222 (2007) doi: 10.1172/JC132169.) Each of these physiological factors poses an opportunity for therapeutic intervention; however, as more has becomes known about individual physiological factors, that knowledge has not always lead to effective therapies because of the complex integration of factors involved in the healing process. (See. e.g., S. A. Eming, P. Martin, and M. Tomic-Canic, "Wound repair and regeneration: mechanisms, signaling, and translation," *Sci. Transl. Med.* 6(265):265sr6. (Dec. 3, 2014) doi: 10.1126/scitranslmed.3009337.) For example, both angiogenesis (sprouting of capillaries from existing blood vessels) and vasculogenesis (mobilization of bone marrowderived endothelial progenitors) contribute to new blood vessel formation during tissue repair. Inadequate local angiogenesis is considered a very likely contributor to the impaired healing of diabetic foot ulcers (DFUs). (Eming et al., 2014.) The therapeutic potential for using vascular endothelial growth factor (VEGF) for vascular therapy was presumed even when it was discovered more than 30 years ago. As of 2014, however, VEGF had not been convincingly used in the clinic to stimulate the growth of functional vessels. (Id.)

The exogenous addition of growth factors nevertheless has shown some limited efficacy in promoting wound healing. For example, fibroblast growth factor 2 [FGF-2; or basic FGF (bFGF)] influences granulation tissue formation, epithelialization, and tissue remodeling and has shown variable results in randomized control clinical trials with favorable outcomes for burn and pressure ulcer healing. Furthermore, keratinocyte growth factor-1 (KGF-1; also known as FGF7), which targets epidermal cells, has been reported to promote healing of skin wounds in mice. (Reviewed in Eming et al., 2014.)

FDA-approved treatments for DFUs and other skin wounds include compositions comprising recombinant human platelet-derived growth factor BB homodimer (rhPDGF-BB), or becaplermin. PDGF isoforms are released by platelets at the site of an injury and exert mitogenic effects on fibroblasts, smooth muscle cells, and other mesenchymal cells. Synthetic rhPDGF-BB participates in the inflammation and granulation tissue stages of wound healing and is an active component of three approved therapeutics: Regranex® Gel, GEM 21S®, and Augment® Bone Graft.

A major stumbling block to the use of growth factor therapy for the treatment of chronic wounds, however, has been the difficulty in protein delivery. (Se U.S. Pat. No. 6,486,133 B1.) These delivery issues have been addressed in U.S. provisional patent application 62/063,793, filed in October 2014, pending U.S. application Ser. No. 15/256,362, filed Sep. 2, 2016, and allowed U.S. application Ser. No. 15/256,339, filed Sep. 2, 2016, which are continuations of PCT International Application Serial No. PCT/US2015/055522, filed Oct. 14, 2014, disclose compositions and methods of treatment comprising rhPDGF-BB. The aforementioned applications are herein incorporated by reference in their entirety.

These applications disclose a biocompatible carrier that effectively delivers the rhPDGFBB to a wound site and simultaneously provides a matrix or scaffold for new cell and tissue ingrowth. The invention provides methods and compositions for treating or promoting the healing of a wound, such as lower extremity ulcers in a diabetic patient, venous stasis ulcers, pressure ulcers, severe burns, and large surgical wounds such as abdominoplasties and other types of surgical tissue flaps. The collagen carrier not only provides a matrix or scaffold for cell ingrowth, but it also absorbs proteases in chronic wound fluid that are detrimental to wound healing. rhPDGF-BB effectively accelerates wound healing by causing an immediate influx of wound healing cells and new blood vessels. The invention overcomes the limitations of an earlier generation products by providing weekly (or less frequent) dosing instead of daily dosing, fewer doses, and a shorter dosing duration, thereby helping patients use the product correctly and potentially improving safety. Improved formulations of rhPDGF-BB are provided that include a carrier that facilitates maintaining an effective dosage at a wound site and provides a substrate for cell and vascular ingrowth. The compositions contain a more potent isoform of PDGF at a higher concentration and fewer less potent isoforms than previous formulations.

Others have specifically designed wound healing therapies using skin substitutes that suppress cytokine-mediated inflammation and granulation tissue formation. The INTEGRA system, for example, uses a two-step procedure to treat full thickness skin wounds. The Integra Dermal Regeneration Template consists of a lower porous dermal component made of bovine type 1 collagen and chondroitin-6-sulphate glycosaminoglycan, which is bonded to an upper silicone pseudo-epidermis. The dermal component of the construct becomes populated with host cells, including fibroblasts, which contribute towards new dermis formation, while the scaffold degrades and the silicone layer protects wounds from moisture loss and bacterial contamination. When the first step is complete (after 14 to 28 days), the silicone layer is peeled off and newly formed neo-dermis is covered with a STSG to achieve final epithelial closure. The chondroitin6-sulphate glycosaminoglycan suppresses the stimulation of the inflammatory response by cytokines, particularly PDGF and TGF γ1.

SUMMARY OF THE INVENTION

The present disclosure combines the wound healing attributes of rhPDGF-BB in a collagen carrier to improve the reliability of graft take, where a skin substitute is used for treating the wound. The invention advantageously improves the treatment of such wounds as lower extremity ulcers in a diabetic patient, venous stasis ulcers, pressure ulcers, severe burns, and large surgical wounds such as abdominoplasties and other types of surgical tissue flaps. The invention thus addresses limitations in both earlier generation growth factor delivery products and skin substitute grafts.

Specifically, the invention provides a method of treating a skin wound, the method comprising:
(1) debriding the wound to remove necrotic or infected tissue;
(2) treating the wound surface by applying a sterile therapeutic composition comprising recombinant human platelet-derived growth factor BB homodimer (rhPDGFBB) and a porous biocompatible carrier to the wound surface, where the sterile therapeutic composition is optionally free from an enzyme inhibitor, the carrier provides a substrate for cell attachment and vascular ingrowth as the wound heals, and said applying delivers at least about 10 µg rhPDGF-BB per $cm^2$ of wound surface area;
(3) optionally covering the wound with a dressing;
(4) optionally using a treatment regimen of repeating steps (1)-(3) for up to 20 times at treatment intervals of three or more days; and
(5) applying a skin-substitute composition to the treated wound.

Steps (1)-(3) may be repeated until granulation tissue covers the treated wound surface, and thereafter the skin-substitute composition may be applied to the newly formed granulation tissue. The sterile therapeutic composition may further comprise a therapeutically effective amount of an angiogenic promoter. The angiogenic promoter, for example, may be selected from the group consisting of a platelet-derived growth factor that is not rhPDGF-BB (PDGF), epidermal growth factor (EGF), fibroblast growth factor (FGF), insulin-like growth factor (IGF), vascular endothelial growth factor (VEGF), transforming growth factor (TGF), keratinocyte growth factor (KGF), hepatocyte growth factor (HGF), stromal cell-derived factor-1α (SDF-1α), interleukin-6 (IL-6), interleukin-8 (IL-8), platelet rich plasma, and combinations thereof. In one embodiment, the angiogenic promoter further comprises IGF or a PDGF that is not rhPDGF-BB.

The skin-substitute composition may comprise living cells, which in one embodiment are stem cells. The stem cells may be selected from the group consisting of mesenchymal stem cells, hematopoietic stem cells, epithelial stem cells, bone marrow stem cells, and adipose-derived stem cells, or combinations thereof. The living cells may comprise epithelial cells, endothelial cells, keratinocytes, fibroblasts, adipose-derived stromal vascular fraction (SVF) cells, and platelets, or combinations thereof. The living cells may comprise cultured cells. For example, the method may comprise applying rhPDGF-BB together with an angiogenic promoter, which may be PDGF and/or IGF, and subsequently applying the skin-substitute composition, which may comprise mesenchymal stem cells, epithelial cells, keratinocytes, or combinations thereof. In some embodiments, the skin-substitute composition comprises an autologous, allogenic, or xenogenic skin graft, which may be a split-thickness skin graft (STSG), full-thickness skin graft (FTSG), or full-thickness skin tissue column (FTSTC), for example. The skin-substitute composition can be applied topically to the wound surface, preferably onto newly formed granulation tissue, by placing, injecting, or spraying the skin-substitute composition onto or into the wound surface or newly formed granulation tissue. In some embodiments, the skin-substitute composition is further supplemented with growth factors appropriate for one or more of the cell types included in the skin-substitute composition.

The therapeutic composition treatment regimen (prior to applying the skin-substitute composition) may last no more than 7, 14, 21, 28, 35, 42, 50, 60, 70, 80, or 90 days, and it may have treatment intervals up to 1, 3, 7, 10, 14, or 21 days, or combinations thereof. For example, the treatment regimen may comprise a single application of the therapeutic composition, followed a few days or weeks later by application of the skin-substitute composition.

The skin wound can be a chronic ulcerated wound, for example, selected from the group consisting of a venous ulcer (VU), venous leg ulcer (VLU), arterial/venous ulcer, arterial ulcer, diabetic foot ulcer (DFU), posttraumatic ulcer, and pressure ulcer. The skin wound can be caused by thermal trauma or surgery, for example. The skin wound can be partial thickness, full thickness, or deeply penetrating into the underlying muscle, fat, bone or other tissues.

The dressing can be a wound dressing comprising a collagen component, analgesic, antibiotic, and/or antiseptic. The antiseptic may be silver, polyhexamethylene biguanide (PHMB), or polyhexadine, for example.

The collagen component may be animal-sourced collagen. It may comprise at least 90% Type 1 collagen, at least 10% type III collagen, hydrolyzed collagen, monomeric collagen, or crosslinked collagen. It may be lyophilized collagen or gel-form collagen.

The skin substitute may comprise a dermal, epidermal, or composite dermo-epidermal cellular component, which may be loaded in vitro or in vivo. The cellular component may be autologous, allogeneic, or xenogeneic. The skin substitute may be covered with a permanent, semi-permanent, or temporary layer. In some embodiments, the skin substitute comprises a biodegradable synthetic component.

The porous biocompatible carrier may comprise collagen, gelatin, fibrin, alginate, cellulose, Chitosan, fibronectin or any synthetic bioabsorbable polymers. It may comprise a collagen sponge or collagen wound dressing. It may comprise an analgesic, antibiotic, and/or antiseptic. The collagen may be animal-sourced collagen. It may comprise at least 90% Type I collagen, at least 10 type III collagen, hydrolyzed collagen, monomeric collagen, or crosslinked collagen. It may be lyophilized collagen or gel-form collagen.

The porous biocompatible carrier can have a pore size distribution of between about 10 microns to about 2,000 microns. It can have an average pore size of between about 50 microns to about 500 microns.

In some embodiments, the sterile therapeutic composition is free from an enzyme inhibitor. In some embodiments, the wound surface area is greater than about 1 cm$^2$.

DETAILED EMBODIMENTS

The presently disclosed compositions and methods advantageously accelerate healing of skin wounds, including skin wounds in which skin substitutes are recommended or required. The advantage of the present method is achieved by applying a sterile therapeutic composition comprising rhPDGF-BB and a porous biocompatible carrier to the wound surface. The skin wound is treated with the therapeutic composition before a skin substitute is applied to the wound to promote mitogenesis, chemotaxis, blood vessel formation, and extracellular matrix and collagen formation, all of which promote a wound environment better suited to facilitate the take of the skin substitute.

Skin Wounds

Skin wounds include those that arise from genetic disorders (bullous conditions), acute trauma, including thermal trauma, chronic wounds, or surgical interventions, such as abdominoplasties and other types of surgical tissue flaps.

Chronic wounds are defined as barrier defects that have not proceeded through orderly and timely reparation to regain structural and functional integrity. Chronic wounds include those that do not heal within three months. Chronic wounds include: (1) vascular ulcers, including venous ulcers (VU), venous leg ulcers (VLUs), arterial/venous, and arterial ulcers; (2) diabetic foot ulcers (DFUs); (3) posttraumatic ulcers; and (4) pressure ulcers.

Granulation tissue is new connective tissue and microscopic blood vessels that form on the surfaces of a wound during the healing process. Granulation tissue typically grows from the base of a wound and is able to fill wounds of almost any size. Granulation tissue is composed of tissue matrix supporting a variety of cell types, most of which can be associated with one of the following functions: formation of extracellular matrix (ECM), operation of the immune system, or vascularization.

Treatable skin wounds may be at least about 1 cm$^2$ in area. Wound area may be less than about 5 cm$^2$, about 5-15 cm$^2$, or over about 15 cm$^2$, up to and including thermal or chemical burns that cover a majority of the body surface area. Ulcerated wounds commonly are located in feet, ankles, legs, buttocks or sacrum areas, and less commonly can be found in the Achilles tendon area, hand, arm, thorax, hip, and other places. Ulcerated wounds that may be treated by the presently disclosed methods include wounds that exceed 1 week, 1 month, 2 months, 6 months, or even 12 months in duration.

Skin wound depth can also vary. Superficial wounds involve the epidermis or the epidermis and papillary dermis. Such injuries do not require specific surgical treatment as only the epidermis is affected and this regenerates rapidly without scarring. Partial thickness wounds penetrate deeply into the dermal layer, with epidermal blistering and severe pain accompanying this type of wound, especially in the case of thermal trauma. Such wounds heal by epithelialization from the margins of the wound, where basal keratinocytes change into a proliferating migratory cell type and cover the damaged area. Cells migrate either from the wound edge, hair follicle, or sweat gland remnants that lie in the deeper dermis. Each hair follicle and sweat gland is lined with epithelial cells capable of contributing to epithelial regeneration across the wounded surface. In addition, the hair follicles of human skin contain a reserve of stem cells, located in the bulge region of the follicle, which are capable of selfrenewal.

Full thickness wounds involve the whole dermal layer with exposure of subcutaneous tissue and are characterized by the complete destruction of epithelial-regenerative elements. This type of injury heals in part by contraction, with epithelialization from only the edge of the wound, leading to cosmetic and functional defects. Full-thickness skin wounds with a diameter of 1 cm or more may require skin grafting because they cannot epithelialize on their own, although skin grafting may be used for partial thickness wounds. Deep wounds penetrate to underlying tissues including tendon, fascia, muscle, and bone. In one embodiment, the methods of treatment are not applied to deep wounds penetrating to bone.

Skin Substitutes

Suitable skin-substitute compositions include skin-substitute products that comprise living cells. The primary locus for loading cellular components into the skin substitute may be in vitro or in vivo. The living cells may comprise epithelial cells, endothelial cells, keratinocytes, fibroblasts, adipose-derived stromal vascular fraction (SVF) cells, and platelets. The living cells may be stem cells or cultured cells. Stem cells may be selected from the group consisting of mesenchymal stem cells, hematopoietic stem cells, epithelial stem cells, bone marrow stem cells, and adipose-derived stem cells. For example, the stem cells may be human CD133$^+$ progenitor cells. (See L. S. Barcelos et al., "Human CD133$^+$ Progenitor Cells Promote the Healing of Diabetic Ischemic Ulcers by Paracrine Stimulation of Angiogenesis and Activation of Wnt Signaling," *Circ Res.* 104(9): 1095-102 (2009).) In one embodiment, the therapeutic composition comprises PDGF and IGF, and the skin-substitute composition comprises mesenchymal stem cells, epithelial cells, keratinocytes, or combinations thereof.

The skin substitute composition may be an autologous, allogenic, or xenogenic skin graft. The autologous, allogenic, or xenogenic skin graft may be a split-thickness skin graft (STSG), full-thickness skin graft (FTSG), or full-thickness skin tissue column (FTSTC). In some embodiments, skin substitutes are biodegradable.

The skin-substitute composition may be applied topically to the wound surface by placing, injecting, or spraying the skin-substitute composition onto the wound surface. In a preferred embodiment, the skin-substitute composition is applied over granulation tissue covering all or part of the treated wound surface. Granulation tissue preferably covers over about 50%, over about 80% or about 100%, of the skin wound in this embodiment.

The skin substitute may be designed to provide permanent, semi-permanent, or temporary cover for a skin wound. The method of the invention thus includes procedures where multiple skin grafts are applied to the skin wound, for example.

Skin substitutes may comprise be epidermal cells, dermal cells, or be composites containing both cell types. Dermo-epidermal or composite skin substitutes aim to mimic the histological structure of normal skin where both epidermal and dermal layers are present. This similarity also provides some functional resemblance to the normal skin. Composite skin substitutes may comprise allogeneic skin cells incorporated into a dermal scaffold. This approach allows the production of large quantities of uniform batches of the product, with a relative 'off-the-shelf' availability. Functionally, these biomaterials may contribute to wound healing by providing growth factors, cytokines, and extracellular matrix (ECM) for host cells. For example, composite skin substitutes may comprise allogeneic keratinocytes to promote effective pain relief and accelerate wound healing. Preferably, composite skin substitutes comprise autologous keratinocytes.

Examples of composite skin substitutes include human viable split-thickness cadaveric allografts, which are used as a temporary measure to cover the wound until it is possible to close it with a permanent skin graft. Allografts have been used for decades and remain the standard for comparison of other temporary skin substitutes. (See W. C. Quinby, J. F. Burke, C. C. Bondoc, "Primary excision and immediate wound closure," *Intensive Care Med.* 7:71-76 (1981).) Another example of a composite skin substitute is Apligraf®, which consists of viable allogeneic neonatal fibroblasts grown in a bovine type I collagen gel matrix, combined with viable allogeneic neonatal keratinocytes, which form a confluent superficial layer of the construct, thus mimicking the normal structure of human skin. (See. e.g., Eaglstein W. H., et al. "Acute excisional wounds treated with a tissue-engineered skin (Apligraf®)," *Dermatol. Surg.* 25:195-201 (1999).) Another example includes OrCell®, a tissue-engineered skin construct that comprises cultured allogeneic fibroblasts and keratinocytes obtained from the neonatal foreskin. Fibroblasts are seeded into a bovine type I collagen sponge, which has a non-porous collagen-gel coating, on top of which keratinocytes are added to form a confluent layer. Being composed of allogeneic cells, the product performs a temporary role, resorbs in 7-14 days (similar to Apligraf®) and no cellular DNA from the product can be found in the wound 14-21 days post-application.

A further example includes the TissueTech Autograft System®, which combines two tissue-engineered biomaterials that are applied consecutively to the wound a dermal replacement construct Hyalograft 3D® and an epidermal substitute Laserskin®. (See Uccioli L. "A clinical investigation on the characteristics and outcomes of treating chronic lower extremity wounds using the TissueTech autograft system." *Int. Low Extrem. Wounds.* 2:140-15 (2003).) These are based on autologous keratinocytes and fibroblasts, grown on microperforated hyaluronic acid membranes. Yet other examples include a three-dimensional reconstructed skin substitute known as PermaDerm®. (See Boyce S. T., Kagan R. J., Greenhalgh D. G., Warner P., Yakuboff K. P., Palmieri T., Warden G. D. "Cultured skin substitutes reduce requirements for harvesting of skin autograft for closure of excised, full-thickness burns." *J. Trauma* 60:821-829 (2006).) PermaDerm® comprises a collagen sponge, which is seeded with autologous fibroblasts and keratinocytes. Additional examples include composite skin substitutes that further comprise endothelial cells, Langerhorn cells, or melanocytes.

Examples of epidermal skin substitutes include those that comprise isolated and cultured keratinocytes. To initiate a culture of autologous cells, a skin biopsy of 2-5 cm$^2$ is usually taken along with initial wound debridement upon the patient's arrival at the clinic. The epidermis is separated from the dermis and single keratinocytes are released from the sheet by exposure to enzymes. These keratinocytes are plated into tissue culture vessels where single cells start to divide to form colonies in the presence of mitotically inactivated mouse fibroblasts and culture medium containing fetal calf serum with necessary supplements. Single colonies of keratinocytes merge together and form stratified epithelial layers which can be enzymatically detached from the culture flasks, mounted onto backing supports (such as paraffin gauze) to maintain basal-apical orientation, and then applied to the wound. Another example is Epicel®, which is indicated for use in adults and pediatric patients who have deep dermal or full thickness burns comprising a total body surface area greater than or equal to 30% It may be used in conjunction with split-thickness autografts, or alone in patients for whom split-thickness autografts may not be an option due to the severity and extent of their burns. Epicel is a cultured epidermal autograft (CEA), a skin graft grown from a patient's own skin. These grafts provide skin replacement for patients who have deep dermal or full thickness burns comprising a total body surface area of greater than or equal to 30%. (It has been claimed that from two postage stamp-sized biopsies, enough epithelium can be grown to cover the patient's entire body.)

Dermal skin substitutes include the Integra Dermal Regeneration Template, which consists of a porous dermal component made of bovine type I collagen and shark chondroitin-6sulphate glycosaminoglycan bonded to a silicone pseudo-epidermis. (Yannas I. V., Burke J. F., "Design of an artificial skin. I. Basic design principles." *J. Biomed. Mater. Res.* 14:65-81 (1980).) The dermal component of the bioconstruct becomes populated with host cells, including fibroblasts, which contribute towards neodermis formation while the material's scaffold degrades, and the pseudo-epidermal component protects wounds from vapor loss and bacterial contamination. When vascularization and neodermis formation are complete, usually within 15-20 days, the silicone layer is peeled off, and the wound can be closed permanently with a split-thickness skin graft.

A major disadvantage of keratinocyte sheet application is the unpredictable clinical outcomes, with varied take rates of 15-85%. (See. e.g., Atiyeh B. S., Costagliola M., "Cultured epithelial autograft (CEA) in burn treatment: three decades later." *Burns* 33:405-413 (2007).) Dermal substitutes likewise suffer from poor and/or unreliable graft take. In one study, cultured epithelial autografts would take in only 15 percent of cases when grafted onto chronic granulation tissue, in 28-47% of cases if grafted onto early granulation tissue or a freshly debrided wound, but would have a 45-75% chance of integration when applied to the wound with a dermal or neodermal bed. (See Orgill D. P., Butler C., Regan J. F., Barlow M. S., Yannas I.V., Compton C. C., "Vascularized collagen-glycosaminoglycan matrix provides a dermal substrate and improves take of cultured epithelial autografts." *Plast. Reconstr. Surg.* 102:423-429 (1998).) The method of the present disclosure advantageously improves the reliability of both keratinocyte and epithelial autografts, among other types of skin substitutes.

Therapeutic Compositions

Provided herein is an improved formulation of rhPDGF-BB that simultaneously includes a combination of the following improvements and benefits: 1) a carrier that facilitates maintaining an effective PDGF dosage at a wound site for an extended period of time; 2) a carrier that provides a substrate for cell attachment and vascular ingrowth; 3) is sterile and therefore safer; 4) is applied less frequently than current therapies, preferably about once every other week, which facilitates better patient compliance and ease of use; 5) has rhPDGF-BB present at a higher concentration than prior art formulations; and 6) contains a more pure and potent rhPDGF-BB formulation with fewer isoforms than certain prior art formulations. In certain embodiments of the invention, all of the above improvements and benefits are simultaneously realized.

Provided herein is a method of treating wounds comprising applying a therapeutic composition to the wound surface, monitoring the healing of the wound, and periodically reapplying the therapeutic composition to the wound surface, if deemed necessary, to achieve healing. In some embodiments, the method further includes debriding the wound to remove necrotic or infected tissue before applying the therapeutic composition and covering the wound with a dressing following the application of the therapeutic composition. In certain embodiments, a semi-occlusive or occlusive dressing is applied over the therapeutic composition, and the dressing may be periodically changed, such as changing the dressing with each reapplication of the therapeutic composition. The method of the present invention may also include the step of cleaning the wound at a dressing change with saline or an appropriate antiseptic wound cleansing agent and/or debriding chemical agent. The methods provided herein may also include treating the patient with a form of infection control or negative pressure wound therapy.

In some embodiments, the method further comprises forming the therapeutic composition by combining sterile PDGF and a sterile biocompatible carrier. The sterile PDGF may be a preformulated sterile PDGF solution or it may be formed as part of the treatment procedure by reconstituting a lyophilized sterile powder containing PDGF with a sterile water or buffer solution. In some embodiments, the biocompatible carrier is a sterile porous matrix that may be selected from the group consisting of natural polymers such as collagen, gelatin, fibrin, alginate, cellulose, or fibronectin. Alternatively, the biocompatible carrier is a sterile porous matrix selected from the group of synthetic polymers such as poly(DL-lactide-co-glycolide) (PLGA), poly(DL-lactide) (PDLA), poly(L-lactide) (PLLA), poly(e-caprolactone) (PCL), polyurethane or others. In some embodiments, the biocompatible carrier is a collagen sponge or a mixture of natural and synthetic polymers.

In some embodiments the therapeutic composition is formed directly on the wound surface by either first applying a carrier, such as a collagen sponge, to the wound surface and then applying a PDGF solution to the collagen sponge, or alternatively by first applying a PDGF solution to the wound surface and then applying a carrier, such as a collagen sponge, to the wound surface. In some embodiments the therapeutic composition is formed by first forming a sterile PDGF solution by reconstituting a lyophilized sterile powder containing PDGF with a sterile water or buffer solution, and then aseptically adding the sterile PDGF solution to a sterile porous biocompatible carrier, such as a collagen sponge, in such a way that the carrier is wetted with the PDGF solution.

In accordance with another aspect of the present invention, there is provided herein a method of treating a dermal wound comprising: debriding the wound; applying a therapeutic composition containing recombinant platelet derived growth factor BB (rhPDGF-BB) to the wound about once every 3 to 42 days for a treatment period of about 2 to about 20 weeks, and wherein said first dose comprises at least about 10 µg of rhPDGF/cm$^2$ of wound surface area; and covering the wound with a dressing following each application of the therapeutic composition. In some embodiment, the method may further comprise advising said patient to avoid applying pressure on the wound as it heals. In some embodiments the cumulative total amount of rhPDGF-BB applied to the wound during the treatment period is less than about 25 mg or about 10 mg or about 5 mg or about 4 mg or about 3 mg or about 2 mg or about 1 mg of rhPDGF-BB. In some embodiments, the method comprises applying the therapeutic composition to the wound once every 7 to 28 days or once every 7 to 21 days or once every 10 to 15 days or once every 12 to 14 days. In some embodiments, each treatment includes application of at least about 10 µg of rhPDGF/cm$^2$ of wound surface area, or between about 10 µg of rhPDGF/cm$^2$ of wound surface area and about 5,000 µg of rhPDGF/cm$^2$ of wound surface area.

The present invention also provides a therapeutic composition comprising sterile PDGF and a biocompatible carrier that may be sterile and/or porous. In some embodiments, the sterile PDGF comprises a pre-formulated sterile PDGF solution, and in other embodiments the sterile PDGF comprises lyophilized sterile powder containing PDGF reconstituted with sterile water or buffer solution.

In certain embodiments, the sterile PDGF included in the therapeutic composition of the present invention comprises an rhPDGF-BB solution containing between about 0.05 mg/ml to about 5 mg/ml of rhPDGF-BB. The rhPDGF-BB solution may be formed by combining a sterile powder containing lyophilized rhPDGF-BB and sterile water or saline, thereby reconstituting the lyophilized rhPDGF-BB into solution. In certain embodiments, the rhPDGF-BB may be produced through an *E. coli* expression system wherein at least about 80% of said rhPDGF-BB on a weight basis is unclipped rhPDGF-BB, which may be subsequently lyophilized. In certain embodiments, the lyophilized rhPDGF-BB is capable of being stored at between about 20° C. and about 26° C. and still maintain the bioactivity of at least 80% of said rhPDGF-BB for at least about six months or at least about one year, or between about 16° C. and about 32° C. and still maintain the bioactivity of at least 80% of said rhPDGF-BB for at least about six months or at least about one year.

In certain embodiments, the carrier included in the therapeutic composition of the present invention may be selected from the group consisting of collagen, gelatin, fibrin, alginate, cellulose, Chitosan, or fibronectin. The carrier may provide a resorbable cell scaffold and may comprise a collagen sponge. In certain embodiments, the carrier that has a pore size distribution of between about 10 microns to about 2,000 microns, and/or an average pore size of between about 50 microns to about 500 microns. In certain embodiments, some of the pores are interconnected or the majority of the pores are interconnected.

Also provided herein is a therapeutic composition comprising an rhPDGF-BB solution and a carrier, such as a matrix, wherein the ratio of the rhPDGF-BB solution to the matrix is between about 4 μl/cm³ to about 40 ml/cm³; or the ratio of rhPDGF-BB to the matrix is between about 1.2 μg PDGF/cm of carrier to about 12 mg PDGF/cm³ of carrier. The rhPDGF-BB solutions disclosed herein may comprise between about 0.05 mg/ml to about 5 mg/ml or between about 0.1 mg/ml to about 1 mg/ml or between about 0.2 mg/ml to about 0.4 mg/ml of rhPDGFBB. The rhPDGF-BB solutions disclosed herein may comprise about 0.3 mg/ml or about 0.5 mg/m; or about 1.0 mg/ml of rhPDGF-BB. In certain embodiments, at least about 80% or about 85% or about 90% or about 95% or about 97% of the rhPDGF-BB included in the PDGF solution or the therapeutic composition on a weight basis is unclipped rhPDGF-BB.

In certain aspects, a therapeutic composition is provided comprising a rhPDGF-BB solution and a carrier, such as a matrix, wherein at least about 20% of the rhPDGF-BB is entrapped within the matrix pores, such that when said composition is applied to a wound on a patient, the rhPDGF-BB is released over time as the matrix is absorbed by the patient's body. In certain embodiments, the therapeutic composition provides sustained delivery of rhPDGF-BB at the wound site as the matrix is resorbed, and simultaneously provides a matrix or scaffold for new cell and tissue ingrowth.

Unless otherwise defined, all technical and scientific terms used herein have the same meaning as commonly understood by one of ordinary skill in the art to which this disclosure belongs. Methods and materials are described herein for use in the present disclosure. Other suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

MODES FOR CARRYING OUT THE INVENTION

The present invention provides for a method of treating wounds, such as diabetic foot ulcers (DFUs), venous stasis ulcers, pressure ulcers, burns, traumatic injuries, and large surgical wounds. The present invention additionally provides for bioactive therapeutic compositions for use in treating such wounds, methods of preparing bioactive carriers useful for the treatment of wounds, and treatment regimens to improve patient compliance and wound healing.

The therapeutic compositions provided herein provide: 1) prolonged delivery of the PDGF onto the wound from each application, thus obviating the need for far more frequent applications by the patient (e.g., daily or every other day applications with prior art products); 2) a physical material, such as a collagen sponge, that can be applied like a Band-Aid® onto the wound once every several days thus improving patient compliance; 3) a sterile product improving safety over prior art products; 4) a higher initial dose of PDGF compared to prior art products which better initiates the healing process thus reducing the need for prolonged patient use; 5) the use of an improved carrier that not only sustains the delivery of the PDGF but simultaneously provides a biological scaffold and/or open porous matrix that facilitates ingrowth of cells, blood vessels and new tissue leading to improved healing compared to prior art products which lack the ability to provide a biological matrix for cellular ingrowth; and 6) contains a more pure and potent rhPDGF-BB formulation with fewer isoforms than prior art formulations. The methods disclosed herein provide: 1) a higher initial dose of PDGF as compared to prior art products to better initiate the healing process, thus reducing the need for prolonged patient use; and 2) a treatment protocol that will facilitate improved patient compliance and convenience by requiring fewer periodic applications of the therapeutic composition, perhaps as few as 1 to 6 applications versus the 140 applications required by prior art products.

Definitions/Nomenclature

As used herein unless otherwise indicated, open terms such as "contain," "containing," "include," "including," and the like mean comprising.

Some embodiments herein contemplate numerical ranges. When a numerical range is provided, the range includes the range endpoints unless otherwise indicated. Unless otherwise indicated, numerical ranges include all values and subranges therein as if explicitly written out.

Some values herein are modified by the term "about." In some instances, the term "about" in relation to a reference numerical value can include a range of values plus or minus 10% from that value. For example, the amount "about 10" can include amounts from 9 to 11. In other embodiments, the term "about" in relation to a reference numerical value can include a range of values plus or minus 10%, 9%, 8%, 7%, 6%, 5%, 4%, 3%, 2%, or 1% from that value.

As used herein, the article "a" means one or more unless explicitly stated otherwise.

Where methods and steps described herein indicate certain events occurring in certain order, those of ordinary skill in the art will recognize that the ordering of certain steps may be modified and that such modifications are in accordance with the variations of the invention. Additionally, certain steps may be performed concurrently in a parallel process when possible, as well as performed sequentially.

The meaning of abbreviations is as follows: "C" means Celsius or degrees Celsius, as is clear from its usage, "μL" or "uL" or "ul" means microliter(s), "mL" means milliliter(s), "L" means liter(s), "mm" means millimeter(s), "nm" means nanometers, "mM" means millimolar, "μM" or "uM" means micromolar, "M" means molar, "mmol" means millimole(s), "μmol" or "uMol" means micromole(s)", "g" means gram(s), "μg" or "ug" means microgram(s) and "ng" means nanogram(s), "% w/v" means weight/volume percent, "% v/v" means volume/volume percent, "HPLC" means high-performance liquid chromatography, "UPLC" means ultraperformance liquid chromatography, and "GC" means gas chromatography.

The term "homology" refers to the optimal alignment of sequences (either nucleotides or amino acids), which may be conducted by computerized implementations of algorithms. "Homology", with regard to polynucleotides, for example, may be determined by analysis with BLASTN version 2.0 using the default parameters. "Homology", with respect to polypeptides (i.e., amino acids), may be determined using a program, such as BLASTP version 2.2.2 with the default parameters, which aligns the polypeptide or fragments (and can also align nucleotide fragments) being compared and determines the extent of amino acid identity or similarity between them. The term "enzyme homolog" can also mean a functional variant.

The above descriptions and methods for sequence homology are intended to be exemplary. Further, it is appreciated that nucleic acid sequences may be varied and still provide a functional enzyme, and such variations are within the scope of the present invention.

As used herein, the term "carrier" is intended to refer broadly to any biologically compatible substance that can serve as a delivery vehicle for PDGF, whereas the terms "matrix" and "scaffold" are used interchangeable to refer to a carrier that acts as a substrate for cell attachment and/or vascular ingrowth as a wound heals, and/or provides a means for trapping the PDGF within its structure (such as, for example, through interconnected pores), thereby allowing for an ongoing or delayed or prolonged delivery of PDGF as a wound heals.

Method of Treating Wounds

The present invention provides methods of treating of skin wounds. In one embodiment, a method of treating a skin wound comprises providing a therapeutic composition comprising a PDGF solution incorporated in a biocompatible carrier, and applying the therapeutic composition to a wound. A therapeutic composition comprising a PDGF solution incorporated in a
biocompatible carrier, for example, can be applied topically to the wound. In some embodiments, a method of treating a wound comprises multiple periodic applications of a therapeutic composition to a wound over a period of weeks.

In accordance with one aspect of the present invention, the treatment method comprises the following steps:
(1) debriding the wound as needed to remove necrotic or infected tissue;
(2) forming a therapeutic composition comprising sterile rhPDGF-BB and a sterile porous biocompatible carrier;
(3) applying the therapeutic composition containing PDGF to the wound surface, wherein the carrier provides a substrate for cell attachment and vascular ingrowth as the wound heals;
(4) optionally covering the wound with a dressing;
(5) monitoring the healing of the wound during a treatment period and repeating steps
(1)-(4) at treatment intervals of 3 or more days, and
(6) applying a skin-substitute composition to the treated wound and optionally covering the skin-substitute composition with a dressing.

Steps (2)-(4) may be repeated until granulation tissue covers at least a portion of the treated wound surface, and thereafter the skin-substitute composition may be applied to the newly formed granulation tissue. The skin-substitute composition can be applied to the newly formed granulation tissue by placing, injecting, or spraying the skin-substitute composition onto or into the wound surface or the newly formed granulation tissue. In accordance with one aspect, the skin-substitute composition may be applied to the peripheral surface of the wound, also by placing, injecting, or spraying onto or into the peripheral surface of the wound. In accordance with an embodiment, the skin-substitute composition is applied when the wound surface area is covered with at least 50%, at least 60%, at least 70%, at least 80%, or at least 90% granulation tissue. In accordance with an embodiment, the skin-substitute composition is applied when the wound cavity is filled with at least 50%, at least 60%, at least 70%, at least 80%, or at least 90% granulation tissue. The method may also include the step of covering the skin-substitute composition with a dressing to minimize movement of the skin-substitute composition, which could interfere with adherence of cells within the skin-substitute composition to granulation tissue, and to maintain moisture.

The treatment method may further include preparing the therapeutic composition prior to applying it to the wound surface, wherein the composition comprises PDGF and a biological carrier. The method of preparing the composition may include:
(1a) reconstituting a lyophilized (freeze-dried) sterile PDGF powder with sterile water, saline, a buffer, or a physiologic solution to provide a specific safe and therapeutic concentration of PDGF; and
(1b) withdrawing the sterile PDGF solution from a vial (container) and aseptically adding it to a dry hydrophilic sterile carrier or patch in such a way that the carrier or patch is wetted with the PDGF solution.

In some embodiments, the dressing is an occlusive or semi-occlusive dressing, or wet-dry gauze, or other commercially available wound dressing. The selection of the dressing type is influenced by the amount of wound exudate, such as using a more absorbent dressing in heavily exudating wounds and a less or non-absorbent dressing over low exudating wounds. In some embodiments, the repeat of steps (1)-(3) may also comprise the steps of: (A) removing the dressing and cleaning the wound with saline or an appropriate antiseptic wound cleansing agent prior to applying the therapeutic composition the dressing, and (B) covering the wound with a new dressing following application of the therapeutic composition.

The dressing promotes recovery of the skin wound by providing a sterile, breathable and moist environment that facilitates granulation and epithelialization and protects the wound from further harm. In various embodiments, the dressing can have a number of purposes, depending on the type, severity, and position of the wound: to help seal the wound to expedite the clotting process; to protect the wound from infection; to protect the wound from mechanical damage; to soak up blood, plasma, and other fluids exuded from the wound; to ease pain, either by a medicated analgesic effect, compression, or preventing pain from further trauma; to remove slough and foreign objects from the wound to expedite healing; and to reduce psychological stress.

The dressing may be separate component of the carrier of the therapeutic composition. In an exemplary embodiment, the dressing may be a component that covers an exposed surface of the therapeutic composition. The dressing then can be removed and replaced separately from the carrier. For example, the dressing can be a bandage, or the dressing can be adhesively connected to the top of the carrier and can be peeled away from the carrier after application to the skin wound. The dressing optionally can then be reapplied to the surface of the implanted carrier. The dressing and carrier also may be integrated components, serving identical roles in the therapeutic method and optionally comprising similar or identical ingredients. In this embodiment, the step of adding a dressing after applying the therapeutic composition to the skin wound is optional.

The dressing and/or carrier, for example, can comprise collagen, such as an animal sourced collagen, gelatin, fibrin, alginate, cellulose, Chitosan, or fibronectin. For example, dressing and/or carrier may comprise a collagen sponge. The collagen may comprise at least 90% Type I collagen, at least 10% type III collagen, hydrolyzed collagen, monomeric collagen, or crosslinked collagen. The collagen may be lyophilized collagen or gel-form collagen. The dressing and/or carrier also can comprise an analgesic, antibiotic and/or antiseptic, such as silver, polyhexamethylene biguanide (PHMB), or polyhexadine.

In some embodiments, bioactive therapeutic compositions described herein may be used in combination with other aspects of treating wounds, including, for example, infection control, negative pressure wound therapy, and/or instructing the patient to avoid placing pressure on the wound site.

In accordance with one aspect of the invention, there is provided a timing schedule for periodically retreating the wound, i.e., repeating steps (2)-(4) or periodically reapplying the therapeutic composition to the wound. The actual number of retreatments and the retreating frequency (i.e., the treatment interval) should be determined based on a number factors, including the severity of the wound (e.g., its grade, size, and depth); the extent to which the natural wound healing environment is compromised (e.g., the vascular supply at the site, the metabolic state of the patient, the ability to off-load pressure on the site, presence of infection, diabetes stage for a DFU, degree of burn for a burn); the patient's age, the duration of the wound; and other co-morbidities, such as smoking, obesity, uncontrolled glucose levels, patient compliance, and others. The number of retreatments and the retreatment frequency should be increased for more severe wounds or for wounds with more compromised healing environments. In addition, the prescribed number of treatments and/or the retreatment frequency may be adjusted during the treatment period based on the wound's rate of healing, i.e., an increased number of retreatments and/or retreatment frequency for slower healing wounds, or a decreased number of retreatments and/or retreatment frequency for faster healing wounds. In some embodiments, a single treatment is sufficient, and retreatment is unnecessary.

In accordance with one aspect of the invention, the retreatment frequency is at least about 2 days, at least about 3 days, at least about 4 days, at least about 5 days, at least about 6 days, at least about 7 days, at least about 8 days, at least about 9 days, at least about 10 days, at least about 11 days, at least about 12 days, at least about 13 days, at least about 14 days, or at least about 15 days and so on up to at least about once every six weeks, or combinations thereof. In accordance with another aspect of the invention, the retreatment frequency is once every 2 to 42 days, or once every 3 to 42 days, or once every 2 to 28 days, or once every 3 to 28 days, or once every 2 to 7 days, or once every 3 to 7 days, or once every 4 to 21 days, once every 7 to 28 days, or once every 7 to 21 days, or once every 7 to 14 days, or once every 10 to 15 days, or once every 12 to 14 days. In accordance with another aspect of the invention, the retreatment frequency is once every 2 days, 3 days, 4 days, 5 days, 6 days, 7 days, 8 days, 9 days, 10 days, 12 days, 14 days, 15 days, 21 days, 28 days, 30 days, 35 days, 42 days, or combinations thereof.

In accordance with one another aspect of the invention, the retreatment frequency is substantially the same over the treatment period, and the retreatment frequency is one time at least about every 2 days, at least about every 3 days, at least about every 4 days, at least about every 5 days, at least about every 6 days, at least about every 7 days, at least about every 8 days, at least about 9 every days, at least about every 10 days, at least about every 11 days, at least about every 12 days, at least about every 13 days, at least about every 14 days, or at least about every 15 days, and so on up to at least about once every six weeks.

In accordance with one aspect of the invention, the wound is retreated at least 1 time, at least 2 times, at least 3 times, at least 4 times, or at least 5 times over the treatment period. In accordance with another aspect of the invention, the wound is retreated between 0 and 6 times, between 0 and 7 times, or between 0 and 8 times over the treatment period. In accordance with another aspect of the invention, the wound is treated between 1 to 8 times, or between 2 to 7 times, or between 3 to 6 times over the treatment period. In accordance with another aspect of the invention, the wound is retreated 1, 2, 3, 4, 5, 6, 7, 8, 10, or 20 times over the treatment period. In accordance with another aspect of the invention the wound is retreated between 0 and 46 times, or between 1 and 46 times, or between 0 and 20 times, or between 1 and 20 times, or between 0 and 27 times, or between 1 and 27 times.

In accordance with one aspect, the skin-substitute composition comprises stem cells, and the method comprises applying a dose of about 1,500 to about 30,000, or about 2,000 to about 25,000, or about 2,500 to about 20,000 stem cells per square centimeter of wound surface. In accordance with another aspect, the overall dosage of stem cells per treatment is about 1 million to about 10 million, or about 3 million to about 8 million, or about 4 million to about 6 million stem cells.

In accordance with another aspect, the skin-substitute composition comprises bone marrow stem cells, which optionally may be harvested from the patient, for example from the patient's bone marrow of the iliac crest. In accordance with this embodiment, bone marrow aspirate is collected from one or both iliac crests, and it is subsequently concentrated, such as through gradient density centrifugation. Preferably, about 150 ml to about 350 ml, or about 200 ml to about 300 ml, or about 220 ml to about 260 ml of bone marrow aspirate is collected, and it is concentrated to about 15% to about 20%° or about 15% to about 18% of its original volume. The resulting bone marrow aspirate concentrate may be applied by injection into the wound site or into a blood vessel adjacent the wound site (e.g., a calf vessel of an ulcerated limb). The bone marrow aspirate may be divided into multiple injections that are applied within and/or around the wound site and/or along an adjacent blood vessel, and preferably each injection is less than 2 ml, or about 0.5 ml to about 1.5 ml, or about 0.75 ml to about 1.25 ml, or about 1 ml.

In accordance with one aspect of the invention, the cumulative total amount of rhPDGFBB applied to the wound during the treatment period is less than about 50 mg, or less than about 25 mg, or less than about 20 mg, or less than about 15 mg, or less than about 10 mg, or less than about 5 mg, or less than about 4 mg, or less than about 3 mg, or less than about 2 mg, or less than about 1 mg of rhPDGF-BB. In certain embodiments, the cumulative total amount of rhPDGF-BB applied to the wound during the treatment period is preferably between about 0.1 mg to about 50 mg, or about 0.5 mg to about 25 mg, or about 1 mg to about 10 mg, or about 2.5 mg to about 8 mg, or about 3 mg to about 7 mg, about 4 mg to about 6 mg.

The various retreatments may involve the same or different dosages of rhPDGF-BB, either in terms of the exact amount of rhPDGF-BB that is applied to the wound (i.e., "absolute dosage") or in terms of the amount of rhPDGF-BB that is applied per square centimeter ($cm^2$) of wound area (i.e., "area dosage"). In accordance with one aspect of the invention, each treatment applies an absolute dosage of between about 10 µg and about 50 mg, or between about 10 µg and about 25 mg, or between about 10 µg and about 20 mg, or between about 10 µg and about 15 mg, or between about 10 µg and about 10 mg, or between about 10 µg and about 5 mg of rhPDGFBB or between about 10 µg and about 1 mg or rhPDGF-BB. In accordance with another aspect of the invention, each treatment applies an area dosage between about 10 µg PDGF/$cm^2$ and about 1.0 mg PDGF/$cm^2$, or between about 10 µg PDGF/$cm^2$ and about 0.5 mg PDGF/ cm², or between about 10 μg PDGF/cm² and about 0.25 mg PDGF/cm², or between about 10 μg PDGF/cm² and 0.1 mg PDGF/cm², or between about 10 μg PDGF/cm² and about 0.05 mg PDGF/cm². In certain embodiments, each treatment with rhPDGF-BB is preferably between about 10 μg to 1000 μg PDGF/cm², or about 0.01 mg to about 50 mg PDGF/cm², or about 0.05 mg to about 25 mg PDGF/cm², or about 0.1 mg to about 10 mg PDGF/cm², or about 0.2 mg to about 2 mg PDGF/cm². In certain embodiments, each treatment applies an area dosage that is at least about 10 μg of rhPDGF/cm² of wound surface area, or at least about 25 μg of rhPDGF/cm: of wound surface area, or at least about 50 μg of rhPDGF/cm² of wound surface area, or at least about 100 μg of rhPDGF/cm² of wound surface area, or at least about 250 μg of rhPDGF/cm² of wound surface area, or at least about 500 μg of rhPDGF/cm² of wound surface area. In certain embodiments, each treatment applies an area dosage that is between about 10 μg of rhPDGF/cm² of wound surface area and about 500 μg of rhPDGF/cm² of wound surface area, or between about 10 μg of rhPDGF/cm² of wound surface area and about 100 μg of rhPDGF/cm² of wound surface area, or between about 15 μg of rhPDGF/cm² of wound surface area and about 375 μg of rhPDGF/cm² of wound surface area, or between about 30 μg of rhPDGF/cm² of wound surface area and about 190 μg of rhPDGF/cm² of wound surface area, or between about 30 μg of rhPDGF/cm² of wound surface area and about 300 μg of rhPDGF/cm² of wound surface area.

In accordance with one aspect of the invention, the initial treatment with compositions in accordance with the present invention may be the most important treatment. PDGF facilitates the wound healing process through its effect on cell proliferation (mitogenesis), directed cellular movement (chemotaxis), and re-vascularization (generating new blood vessels). Many cells have been shown to possess receptors (binding sites) for PDGF, including connective tissue cells (skin, bone, cartilage, tendon and ligament), blood vessel cells, and cells of the nervous system. Cells that possess receptors for PDGF respond by migrating toward the site of the wound (where PDGF is present at elevated levels as a result of applying therapeutic compositions in accordance with the present invention) and subsequently proliferating after binding PDGF. Since the PDGF receptor is degraded quickly after activation, cell proliferation is controlled and limited by the presence of locally available PDGF, as well as by cell-cell interactions that lead cells to proceed from the proliferative phase of wound healing to that of matrix deposition, which ultimately results in complete healing. As a result, a critical bolus of rhPDGF-BB must be applied during the initial treatment to ensure that the patient's natural wound healing process is properly activated. Therefore, in accordance with the invention, the initial treatment comprises applying a therapeutic composition containing an area dosage that is at least 10 μg PDGF/cm² wound surface area, up to 5000 μg PDGF/cm² wound surface area, or at least 20 μg PDGF/cm² up to 1000 μg PDGF/cm² wound surface area, or at least 30 μg PDGF/cm² up to 600 μg PDGF/cm² wound surface area, or at least 40 μg PDGF/cm² up to 400 μg PDGF/cm² wound surface area, or at least 50 μg PDGF/cm² up to 350 μg PDGF/cm² wound surface area, or at least 60 μg PDGF/cm² up to 300 μg PDGF/cm² wound surface area, or at least 200 μg PDGF/cm² up to 2000 μg PDGF/cm² wound surface area. In accordance with another aspect of the invention, the initial treatment comprises applying a therapeutic composition containing an area dosage that is at least 10 μg PDGF/cm² wound surface area, or at least 20 μg PDGF/cm² wound surface area, or at least 25 μg PDGF/cm² wound surface area, or at least 30 μg PDGF/cm² wound surface area, or at least 40 μg PDGF/cm² wound surface area, or at least 50 μg PDGF/cm² wound surface area, or at least 60 μg PDGF/cm² wound surface area, or at least 70 μg PDGF/cm² wound surface area, or at least 80 μg PDGF/cm² wound surface area, or at least 90 μg PDGF/cm² wound surface area, or at least 100 μg PDGF/cm² wound surface area, or at least 250 μg PDGF/cm² wound surface area, or at least 500 μg PDGF/cm² wound surface area.

In accordance with another aspect of the invention, each treatment applies is between about 4 μl PDGF solution/cm³ of carrier (which may be a matrix, such as a collagen sponge) to about 40 ml PDGF solution/cm³ of carrier, or between about 0.1 ml PDGF solution/cm³ of carrier to about 30 ml PDGF solution/cm³ of carrier, or between about 0.2 ml PDGF solution/cm³ of carrier to about 20 ml PDGF solution/cm³ of carrier, or between about 0.1 ml PDGF solution/cm³ of carrier to about 10 ml PDGF solution/cm³ of carrier, or between about 0.25 ml PDGF solution/cm³ of carrier to about 5 ml PDGF solution/cm³ of carrier, or between about 0.25 mil PDGF solution/cm³ of carrier to about 2.5 mil PDGF solution/cm³ of carrier, or between about 0.1 ml PDGF solution/cm³ of carrier to about 1 ml PDGF solution/cm³ of carrier, or between about 0.5 ml PDGF solution/cm³ of carrier to about 1.5 ml PDGF solution/cm³ of carrier. In certain embodiments, the PDGF solution contains about 0.3 mg/ml of rhPDGF-BB.

In accordance with another aspect of the invention, each treatment applies between about 1.2 μg PDGF/cm³ of carrier to about 12 mg PDGF/cm³ of carrier, or between about 30 μg PDGF/cm³ of carrier to about 9 mg PDGF/cm³ of carrier, or between about 60 PDGF/cm³ of carrier to about 6 mg PDGF/cm³ of carrier, or between about 75 μg PDGF/cm³ of carrier to about 3 mg PDGF/cm³ of carrier, or between about 75 μg PDGF/cm³ of carrier to about 1.5 mg PDGF/cm³ of carrier, or between about 75 μg PDGF/cm³ of carrier to about 750 μg PDGF/cm³ of carrier, or between about 120 μg PDGF/cm³ of carrier to about 600 μg PDGF/cm³ of carrier, or between about 150 μg PDGF/cm³ of carrier to about 450 μg PDGF/cm³ of carrier, or between about 75 μg PDGF/cm³ of carrier to about 225 μg PDGF/cm³ of carrier.

In accordance with one aspect of the invention, the initial PDGF treatment absolute dosage may be greater than the subsequent retreatment dosages. The initial PDGF treatment absolute dosage may be about 10%, about 20%, about 30%, about 40%, or about 50% higher, or up to about 300% higher than each of the subsequent retreatment PDGF dosages.

In accordance with one aspect of the invention, the method includes storing the PDGF at room temperature, generally between 16 and 32° C. Prior to use it may be reconstituted with sterile water, saline, a buffer, or other physiologic solution to form a solution having the desired PDGF concentration. The solution is then added to a carrier, preferably a cell matrix (e.g., a collagen sponge) having the desired porosity in the desired volume to wet the matrix. The rhPDGF-soaked matrix is then applied to the wound surface. If the wound is an external wound, it is then covered with a wound dressing. This process may then be repeated in accordance with frequency and duration parameters described above until the wound is substantially healed.

Therapeutic Compositions for Treating Wounds

The present invention also provides therapeutic compositions for treating wounds, which comprise sterile PDGF incorporated in a biocompatible sterile carrier, matrix or scaffold. For example, the therapeutic composition can be applied topically to a wound to facilitate the wound's healing.

In accordance with one aspect of the invention, a therapeutic composition is provided that comprises a rhPDGF-BB solution and a carrier that is preferably a biocompatible cell scaffold, wherein the rhPDGF-BB solution is disposed in or incorporated into the cell scaffold. In some embodiments, the rhPDGF-BB solution comprises between about 0.05 mg/ml to about 5 mg/ml of rhPDGF-BB, or between about 0.1 mg/ml to about 1 mg/ml of rhPDGF-BB, or between about 0.2 mg/ml to about 0.4 mg/ml of rhPDGF-BB. In accordance with one aspect of the invention, the rhPDGF-BB solution contains rhPDGF-BB at a concentration of about 0.05 mg/ml, or about 0.1 mg/ml, or about 0.2 mg/ml, or about 0.25 mg/ml, or about 0.3 mg/ml, or about 0.35 mg/ml, or about 0.4 mg/ml, or about 0.5 mg/ml, or about 0.6 mg/ml, or about 0.7 mg/ml, or about 0.8 mg/ml, or about 0.9 mg/ml, or about 1 mg/ml, or about 2 mg/ml, or about 3 mg/ml, or about 4 mg/ml, or about 5 mg/ml.

In some embodiments, the rhPDGF-BB solution is a preformulated aseptic PDGF solution comprising the elements described herein (e.g., PDGF concentration, sterile solution composition, etc.). In other embodiments the rhPDGF-BB solution is formed at the time of use, preferably by combining a sterile solution (e.g., sterile water, saline, a buffer solution, or a physiologic solution) with a sterile powder comprising or consisting essentially of lyophilized rhPDGF-BB. The sterile solution is used to reconstitute the lyophilized rhPDGF-BB. The lyophilized rhPDGF-BB is formed by lyophilizing liquid rhPDGF-BB produced by using a recombinant expression system as described further herein below under aseptic conditions.

In another aspect of the invention rhPDGF may be incorporated into carrier, preferably a sterile, biocompatible, absorbable cell scaffold, and the PDGF saturated carrier is then lyophilized to form a sterile, dry device incorporating rhPDGF. Any known technique for lyophilizing recombinant proteins may be used to lyophilize rhPDGF-BB so long as it yields a sterile powder. The resulting lyophilized rhPDGF-BB powder is capable of being stored at room temperature and still maintain at least about 80% of its bioactivity for at least about 6 months, or at least about 1 year, or at least about 2 years, or at least about 3 years. The sterile lyophilized device may then be applied directly to a wound site or wetted either by blood or other sterile solution prior to placement on the wound.

Because PDGF has a tendency to adhere to surfaces of a container, such as a vial, (particularly at higher pH's) achieving reconstitution of 100% of the lyophilized PDGF in a vial may be challenging. Therefore, in certain embodiments, additives may be included in the PDGF solution to lower its pH below about 7, or below about 6, or below about 5 or below about 4 or below about 3. Additives that may facilitate reconstituting the lyophilized PDGF include salts, carrier proteins such as albumin, or low pH solutions, such as dilute acetic acid or hydrochloric acid. If the PDGF solution is too acidic, however, it could negatively impact the biocompatible scaffold. Therefore, in certain embodiments, the lyophilized PDGF is reconstituted in a solution having a pH below about 5, and once the PDGF is substantially fully reconstituted, a base solution is added to increase the pH of the PDGF solution to between about 6 to about 8, or to increase it to about 7 before it is combined with the biocompatible scaffold. Such a pH adjustment step is particularly useful when the biocompatible scaffold is a collagen sponge.

The buffer solution used to reconstitute the lyophilized rhPDGF-BB may comprise, but is not limited to, water, saline, carbonates, phosphates (e.g. phosphate buffered saline), histidine, acetates (e.g. sodium acetate), acidic buffers such as acetic acid and HCl, and organic buffers, such as lysine, Tris buffers (e.g. tris(hydroxymethyl)aminoethane), N-2-hydroxyethylpiperazineN'-2-ethanesulfonic acid (HEPES), and 3-(N-morpholino) propanesulfonic acid (MOPS).

Preferably, the buffer solution is sterile. Buffers can be selected based on biocompatibility with PDGF and the buffer's ability to impede undesirable protein modification. Buffers can additionally be selected based on compatibility with wound tissues. In one embodiment, sodium acetate buffer is used. The buffers can be employed at different molarities, for example, about 0.1 mM to about 100 mM, about 1 mM to about 50 mM, about 5 mM to about 40 mM, about 10 mM to about 30 mM, or about 15 mM to about 25 mM, or any molarity within these ranges. In some embodiments, an acetate buffer is employed at a molarity of about 20 mM.

As noted above, the rhPDGF-BB solution is combined with a carrier to form a therapeutic composition. The carrier may be a matrix or scaffold that acts as a substrate for cell attachment and/or vascular ingrowth as a wound heals, and/or provides a means for trapping the PDGF within its structure (such as, for example, through interconnected pores), thereby allowing for an ongoing or delayed or prolonged delivery of PDGF as a wound heals and the matrix or scaffold is resorbed by the body. In some embodiments, the carrier or matrix is a biocompatible, resorbable cell scaffold. The carrier or matrix may comprise natural polymers such as collagen, gelatin, fibrin, alginate, cellulose, Chitosan, or fibronectin. The carrier or matrix may also comprise synthetic biocompatible polymers selected from the group of synthetic polymers such as poly(DL-lactide-co-glycolide) (PLGA), poly(DL-lactide)(PDLA), poly(L-lactide)(PLLA), poly(e-caprolactone)(PCL), polyurethane or others. The carrier or matrix may also be a mixture of such natural and synthetic polymers. In some embodiments, the matrix comprises a collagen or gelatin sponge, which may be a Type I collagen sponge. A collagen sponge holds the rhPDGF at the wound site and concurrently provides a scaffold for cell growth, resulting in improved user friendliness and more rapid and complete healing. In one aspect the invention, the carrier or matrix, which may be a collagen sponge, has a porosity of between about 10 microns to about 2 mm, or about 50 microns to about 1000 microns, or about 100 microns to about 500 microns. The average pore size may be between about 50 microns to about 500 microns and wherein the majority of the pores are interconnected.

In some embodiments, carrier or matrix materials are bioresorbable. A carrier or matrix material, in one embodiment, can be at least 20%, 30%, 40%, 50%, 60%, 70%, 75%, 90%, or 100% resorbed within one month subsequent to its application to the wound. Resorption will be dependent on: (1) the nature of the material (i.e., its chemical makeup, physical structure and size); (2) the location within the body in which the material is placed; (3) the amount of material that is used, (4) the metabolic state of the patient (diabetic/non-diabetic, smoker, age, etc.); and (5) the extent and/or type of wound treated.

In one aspect of the invention, the rhPDGF-BB solution and the carrier should be combined in an appropriate ratio in order to form a therapeutic composition that has optimal effectiveness in healing wounds. In some embodiments, the rhPDGF-BB solution and the carrier are combined at a ratio that is between about 4 µl PDGF solution/cm³ of carrier (which may be a matrix, such as a collagen sponge) to about 40 µl PDGF solution/cm³ of carrier, or between about 0.1 ml PDGF solution/cm³ of carrier to about 30 ml PDGF solution/cm³ of carrier, or between about 0.2 ml PDGF solution/cm³ of carrier to about 20 ml PDGF solution/cm³ of carrier, or between about 0.1 ml PDGF solution/cm³ of carrier to about 10 ml PDGF solution/cm³ of carrier, or between about 0.25 ml PDGF solution/cm³ of carrier to about 5 ml PDGF solution/cm³ of carrier, or between about 0.25 ml PDGF solution/cm³ of carrier to about 2.5 ml PDGF solution/cm³ of carrier, or between about 0.1 ml PDGF solution/cm³ of carrier to about 1 ml PDGF solution/cm³ of carrier, or between about 0.5 ml PDGF solution/cm³ of carrier to about 1.5 ml PDGF solution/cm³ of carrier.

In some embodiments, the rhPDGF-BB and the carrier are combined at a ratio that is between about 1.2 µg PDGF/cm³ of carrier to about 12 mg PDGF/cm³ of carrier, or between about 30 µg PDGF/cm³ of carrier to about 9 mg PDGF/cm³ of carrier, or between about 60 µg PDGF/cm³ of carrier to about 6 mg PDGF/cm³ of carrier, or between about 75 µg PDGF/cm³ of carrier to about 3 mg PDGF/cm³ of carrier, or between about 75 µg PDGF/cm³ of carrier to about 1.5 mg PDGF/cm³ of carrier, or between about 75 µg PDGF/cm³ of carrier to about 750 µg PDGF/cm³ of carrier, or between about 120 µg PDGF/cm³ of carrier to about 600 µg PDGF/cm³ of carrier, or between about 150 µg PDGF/cm³ of carrier to about 450 µg PDGF/cm³ of carrier, or between about 75 µg PDGF/cm³ of carrier to about 225 µg PDGF/cm³ of carrier.

In one aspect of the invention, the carrier is a scaffold and the rhPDGF-BB/scaffold ratio is such that when the rhPDGF-BB solution and the scaffold are combined, the scaffold is capable of entrapping at least about 20%, 30%, 40% or 50% up to at least about 100% of the rhPDGFBB within the scaffold's pores such that the rhPDGF-BB is released over time as the scaffold is absorbed by the patient's body, thereby providing controlled delivery of rhPDGF-BB at the wound site over an extended period of time and simultaneously providing a matrix for new cell and tissue ingrowth. In some embodiments, the scaffold is capable of entrapping between about 20% to about 100%, or between about 25% to about 95%, or between 30% to about 90% of the rhPDGF-BB within the scaffold's pores. The percentages of PDGF entrapment described above are also applicable to entrapment of reconstituted lyophilized PDGF-BB.

Various amounts of rhPDGF-BB may be used in the therapeutic compositions of the present invention. In accordance with one aspect of the invention, the total amount of rhPDGFBB included in the therapeutic composition is less than 50 mg, or less than 25 mg, or less or less than 10 mg, or less than 5 mg, or less than 2.5 mg or less than 1 mg. In accordance with another aspect of the invention the total amount of rhPDGF-BB included in the therapeutic composition is about 50 mg, or about 25 mg, or about 10 mg, or about 1.0 mg, or about 0.5 mg, or about 0.1 mg.

The concentration of PDGF in embodiments of the present invention can be determined by using an enzyme-linked immunoassay as described in U.S. Pat. Nos. 6,221,625, 5,747,273, and 5,290,708 or any other assay known in the art for determining PDGF concentration. The concentration of PDGF in the embodiments of the present invention is less than about 10 mg/g, or less than about 5 mg/g or less than about 1 mg/g or less than about 0.5 mg/g or less than about 0.1 mg/g or less than about 0.05 mg/ml. In another aspect of the invention the concentration of PDGF in the embodiments of the present invention is between about 0.05 mg/g to about 5 mg/g, or between about 0.1 mg/g to about 1 mg/g or between about 0.25 mg/g and about 0.5 mg/g.

The PDGF-BB used in the therapeutic composition of the present invention may be derived from any source such as natural source, synthetic source, or recombinant source. In accordance with one aspect of the invention, PDGF is produced by recombinant DNA techniques. When PDGF is produced by recombinant DNA techniques, a DNA sequence encoding a single monomer (e.g., PDGF B-chain), is inserted into cultured cells for expression of the B chain monomer. The monomer is then extracted and isolated from the cell culture and refolded to form the biologically active homodimer (e.g., PDGF-BB), which may be further processed for additional purification. In accordance with one aspect of the invention, the cultured cells are prokaryotic cells or are E. coli cells. The rhPDGF-BB produced through these recombinant techniques can be purified in accordance with the techniques outlined in PCT No. WO 2005/077973, for example.

In accordance with one aspect of the invention, substantially all of the rhPDGF-BB included in the therapeutic compositions described herein are intact non-clipped chains. In accordance with one aspect of the invention, the bacterial expression system is an E. coli expression system, and the resulting protein is purified using reversed phase high performance liquid chromatography, gel filtration, or ion exchange chromatography, or some combination thereof, wherein the resulting rhPDGF-BB contained in the purified protein composition is at least about 80%, or at least about 85%, or at least about 90%, or at least about 95%, or at least about 97% unclipped rhPDGF-BB on a weight basis.

In some embodiments, the rhPDGF-BB included in the therapeutic compositions of the present invention is a rhPDGF-BB that comprises or consists essentially of an amino acid sequence having at least about 99% or 100% homology to SEQ ID NO. 1, which is provided below:

```
SEQ ID NO. 1:
Ser Leu Gly Ser Leu Thr Ile Ala Glu Pro Ala Met Ile Ala Glu Cys Lys Thr Arg Thr
                5                   10                  15                  20

Glu Val Phe Glu Ile Ser Arg Arg Leu Ile Asp Arg Thr Asn Ala Asn Phe Leu Val Trp
                25                  30                  35                  40

Pro Pro Cys Val Glu Val Gln Arg Cys Ser Gly Cys Cys Asn Asn Arg Asn Val Gln Cys
                45                  50                  55                  60

Arg Pro Thr Gln Val Gln Leu Arg Pro Val Gln Val Arg Lys Ile Glu Ile Val Arg Lys
                65                  70                  75                  80
```

```
-continued
Lys Pro Ile Phe Lys Lys Ala Thr Val Thr Leu Glu Asp His Leu Ala Cys Lys Cys Glu
                85                  90                  95                 100

Thr Val Ala Ala Ala Arg Pro Val Thr
                105
``` rhPDGF-BB analogues that are known in the art to function like the rhPDGF-BB of SEQ ID NO: 1 include the PDGF-B(C2,QS) analog disclosed in W. C. Kenney et al., "Formation of Mitogenically Active PDGF-B Dimer Does Not Require Interchain Disulfide Bond," *J. Biol. Chem.* 269: 12351-59 (1994) and the GP4 peptide disclosed in U.S. Pat. No. 6,350,731 B1.

In accordance with another aspect of the invention, the rhPDGF-BB included in the therapeutic compositions of the present invention comprises or consists essentially of at least about 80%, or at least about 85%, or at least about 90%, or at least about 95%, or at least about 97% unclipped rhPDGF-BB on a weight basis. In accordance with another aspect of the invention, the rhPDGF-BB included in the therapeutic compositions of the present invention comprises or consists essentially of at least about 80%, or at least about 85%, or at least about 90%, or at least about 95%, or at least about 97% of rhPDGF-BB that comprises or consists essentially of an amino acid sequence having at least about 90%, about 91%, about 92%, about 93%, about 94%, about 95%, about 96%, about 97%, about 98%, about 99%, or about 100% homology to SEQ ID NO 1.

In some embodiments, the compositions of the present invention are provided in a kit. A kit can comprise three components.
a) a vial of sterile rhPDGF-BB lyophilized powder,
b) a vial of sterile water, a buffer, saline, or a physiologic solution, and c) a carrier.

The kit may be stored at room temperature for up to 3 years. In some embodiments the storage is between 16 and 32° C. In some embodiments, the powder included in the kit comprises a predetermined amount of PDGF. In some embodiments, the amount of PDGF is consistent with the values provided herein. In some embodiments, the carrier is included in a blister pack comprising a predetermined amount of carrier. In some embodiments, the amount of carrier is consistent with the values provided herein, and the type carrier is consistent with the materials described herein.

In one embodiment, the rhPDGF-BB in the kit is reconstituted with the sterile water, saline, buffer, or physiologic solution, and the carrier is shaped to the size of the wound. Following trimming the carrier to fit the wound, it is soaked with the rhPDGF solution, such that the solution fully saturates the interior pores of the carrier. The rhPDGF-saturated carrier is then applied to the debrided wound and covered with a wound dressing. This process may be repeated in accordance with the timing schedules described hereinabove.

Methods of Treating Various Types of Wounds

The methods and compositions of the present invention are useful in treating a variety of wounds including diabetic ulcers, pressure ulcers, neuropathic ulcers, vascular ulcers, burns, accidental acute wounds and surgical wounds. Various wound classification systems exists and can be used to identify wounds that methods and compositions of the present invention are particularly useful in treating. Two such ulcer classification systems include the Wagner classification system (see, Wagner (1987) Orthopedics 10:163-72) and the University of Texas classification system (see, Lavery (1996) J Foot Ankle Surg 35:528-31). The Wagner system grades the wound by the depth of the wound and the presence of infection. It has five numeric grades:
Grade 1: Superficial diabetic ulcer
Grade 2: Ulcer extension
Involves ligament, tendon, joint capsule or fascia
No abscess or osteomyelitis
Grade 3: Deep ulcer with abscess or osteomyelitis
Grade 4: Gangrene to portion of forefoot
Grade 5: Extensive gangrene of foot The University of Texas classification system has four numeric grades based on the depth of the wound. In addition, there are four letter grades, A to D, related to infection and ischemia. The University of Texas classification system includes:
Stages
Stage A: No infection or ischemia
Stage B: Infection present
Stage C: Ischemia present
Stage D: Infection and ischemia present
Grading
Grade 0: Epithelialized wound
Grade 1: Superficial wound
Grade 2: Wound penetrates to tendon or capsule
Grade 3: Wound penetrates to bone or joint A wound with a numeric grade of 3 and letter grade of D, for example, would be a wound that penetrates to a bone or joint and is infected and ischemic. In accordance with one aspect of the present invention, the methods and compositions of the present invention are used to treat a wound that is either a grade 2, grade 3, or grade 4 wound under the Wagner classification system, or a grade 1, 2, or 3 wound (stages A, B, C, or D) under the University of Texas classification system. In one embodiment, the skin wound is a Grade 2 (stage A-D) wound under the University of Texas classification system.

In some embodiments, the methods and compositions described herein may be used to treat wounds such as lower extremity ulcers, and in particular foot ulcers on diabetic patients. The methods and compositions of the present invention are particularly useful in treating nonhealing lower extremity diabetic ulcers which have failed to heal by about 50% after about 4 weeks of conventional therapies under the current standard of care as described above in the Background.

In some embodiments, the compositions of the present invention are used to treat burns. In one embodiment, the compositions are used in combination with a 1:1.5 or 1:1.3 meshed split thickness skin graft (the meshing allows the graft to cover a wider area but leaves small openings that need to heal), abdominoplasties (so-called "tummy tucks"), healing following other types of plastic and reconstructive surgeries, or post-amputation wounds.

Additional Therapeutic Elements

The therapeutic compositions of the present invention may include additional therapeutics elements to further facilitate healing a wound. In some embodiments, solutions comprising PDGF can further comprise additional components, such as other biologically active agents. In other embodiments, solutions comprising PDGF can further comprise cell culture media, other stabilizing proteins such as albumin, antibacterial agents, protease inhibitors [e.g., ethylenediaminetetraacetic acid (EDTA), ethylene glycol-bis(beta-aminoethylether)-N,N,N',N'tetraacetic acid (EGTA), aprotinin, 8-aminocaproic acid (EACA), etc.] and/or other growth factors such as fibroblast growth factors (FGFs), epidermal growth factors (EGFs), transforming growth factors (TGFs), keratinocyte growth factors (KGFs), insulin-like growth factors (IGFs), or other PDGFs including compositions of PDGF-AA, PDGF-BB, PDGF-AB, PDGF-CC and/or PDGF-DD. In addition, biologically active agents that can be incorporated into compositions of the present invention in addition to PDGF can comprise organic molecules, inorganic materials, proteins, peptides, nucleic acids (e.g., genes, gene fragments, small insert ribonucleic acids (siRNAs), gene regulatory sequences, nuclear transcriptional factors, and antisense molecules), nucleoproteins, polysaccharides (e.g., heparin), glycoproteins, and lipoproteins. Additional nonlimiting examples of biologically active compounds that can be incorporated into compositions of the present invention, including, e.g., anti-cancer agents, antibiotics, analgesics, antiinflammatory agents, immunosuppressants, enzyme inhibitors, antihistamines, hormones, muscle relaxants, prostaglandins, trophic factors, growth factors, and vaccines, are disclosed in U.S. patent application Ser. No. 11/159,533 (Publication No: 20060084602).

Standard protocols and regimens for delivery of additional biologically active agents are known in the art. Additional biologically active agents can be introduced into compositions of the present invention in amounts that allow delivery of an appropriate dosage of the agent to the wound site. In most cases, dosages are determined using guidelines known to practitioners and applicable to the particular agent in question. The amount of an additional biologically active agent to be included in a composition of the present invention can depend on such variables as the type and extent of the condition, the overall health status of the particular patient, the formulation of the biologically active agent, release kinetics, and the ability of the biocompatible scaffold to be resorbed. Standard clinical trials may be used to optimize the dose and dosing frequency for any particular additional biologically active agent.

EXAMPLES

Example 1

The efficacy of a collagen wound dressing containing 0.3 mg/ml recombinant human platelet derived growth factor-BB homodimer (rhPDGF-BB) was evaluated in the treatment of surgically induced full-thickness wounds in mice rendered diabetic by a mutation in the leptin receptor (db/db).

A. Study Design

Fifteen (15) male C57/B6 (Leprdb) db/db mice with an average starting body weight of 41.46 g were obtained from Jackson Laboratory (Bar Harbor, Me.) strain code 000642. Animals were acclimatized prior to study commencement. During this period of 3 days, the animals were observed daily in order to reject animals that presented in poor condition.

During the study all animals were single housed under identical conditions in disposable cages. The study was performed in animal rooms provided with HEPA-filtered air at a temperature of 70° F.+5° F. and relative humidity of 50%+20%. Animal rooms were set to maintain a minimum of 12 to 15 air changes per hour. The room was on an automatic timer for a light/dark cycle of 12 hours on and 12 hours off with no twilight. AlphaDry™ bedding was used. Bedding was changed a minimum of once per week. Cages, tops, bottles, etc. were washed with a commercial detergent and allowed to air dry. A commercial disinfectant was used to disinfect surfaces and materials introduced into the hood. Floors were swept daily and mopped a minimum of twice weekly with a commercial detergent. Walls and cage racks were sponged a minimum of once per month with a dilute bleach solution. A cage card or label with the appropriate information necessary to identify the study, dose, animal number and treatment group marked all cages. The temperature and relative humidity was recorded during the study, and the records retained. Animals were fed with a sterile Purina Labdiet™ 5053 rodent diet and sterilized water was provided ad libitum.

At the commencement of the study, the fifteen (15) animals were randomly and prospectively divided into three (3) groups of five (5) animals each:

Group 1: Regranex® Gel 0.01% rhPDGF-BB was applied daily for 21 days as prescribed by the package insert;

Group 2: A collagen wound dressing combined with buffer was applied on days 0, 7, and 14; and Group 3: A collagen wound dressing containing 0.3 mg/ml recombinant human platelet derived growth factor-BB (rhPDGF-BB) was applied on days 0, 7, and 14.

Each animal was identified by an ear punch corresponding to an individual number. On Day 0, mean starting weights were recorded to ensure that mean starting weights were comparable among groups. A cage card was used to identify each cage or label marked with the study number (LYN-01), treatment group number, and animal numbers.

Test and control collagen±PDGF articles were administered topically as surgical dressings (as described below) immediately following the induction of the wound and were changed every seven (7) days. Regranex®-treated sites were treated as prescribed in the Instructions For Use (IFU) included in the product insert, including daily dosing as outlined below. All dressings were applied and held in place using Tegaderm™ and secured in place outside of the wound area with benzoin. At the time of dressing change, the wound area was rinsed with saline and the rinse was collected and stored at −80° C. for future analysis of protease activity. For sites treated with the collagen wound dressing, all non-adherent collagen was gently removed from the healing wound, the site rinsed with saline, and the rinse collected as described. Following removal of the dressing and collection of the rinse, the wound was measured using a caliper and photographed prior to re-application of dressing/test article. All wound areas were reported in mm$^2$.

For photographic documentation of wound healing, the camera was mounted on a tripod at an optimal distance to ensure all photos were consistent A ruler was placed such that it was captured in the image to allow accurate estimation of lesion size. In addition to live measurements of the wound area, all photographs of the wounds were analyzed using Image J Software®, and the wound area was traced and quantitated at the conclusion of the study.

Blood glucose levels were determined prior to the start of the study and again just prior to sacrifice on Day 21 to confirm diabetic disease state. At study termination, the wound site was collected in 10% NBF and prepared for histopathology. The study design is summarized below in Table 1.

TABLE 1

Study Design

| Group Number | Number of Animals | Wound (Day 0) | Treatment* | Route/ Frequency | Wound Assessment |
|---|---|---|---|---|---|
| 1 | 5 male (db/db) | 1.5 cm × 1.5 cm | Regranex Gel | Topical- 21 daily applications; dose applied based on open wound measurements at Day 0, 7 and 14*** | Daily To Day 21 |
| 2 | 5 male (db/db) | 1.5 cm × 1.5 cm | Collagen wound dressing + Buffer | Topical- 3 weekly applications; Days 0, 7 and 14*** | Every 7 Days To Day 21 |
| 3 | 5 male (db/db) | 1.5 cm × 1.5 cm | PDGF Bioactive Wound Dressing | Topical - 3 weekly applications; Days 0, 7 and 14*** | Every 7 Days To Day 21 |

*All dressings were applied and held in place by Tegaderm™
**The cm length of Regranex applied was based on open wound measurements obtained on Days 0, 7 and 14. The centimeter length of Regranex applied daily was the same for Days 0-6 and was based on measurements obtained on Day 0. The centimeter length of Regranex applied daily for Days 7-13 was based on measurements obtained on Day 7 and the centimeter length of Regranex applied on Days 14-21 was based on measurements obtained on Day 14. See "PDGF-BB Calculations" for detail.
***The volume of PDGF-BB or buffer/sterile saline that was applied to the collagen sponge at Days 0, 7 and 14 utilized the formula: 145 × cm² open wound surface area (length [cm] × width [cm] open wound)

B. Test Articles & Vehicle Preparation

The topical formulations used in the study were Regranex® Gel (0.01% rhPDGF-BB in carboxymethylcellulose gel) (Group 1); a collagen wound dressing wetted with rhPDGF-BB (Group 3); and a collagen wound dressing wetted with saline (Group 2). All dressings were covered with Tegaderm™ and secured with benzoin.

1. Dressing Compositions a. Group 1 rhPDGF Dosage

As described in Regranex Package Insert, "each square centimeter of ulcer surface area will require approximately 0.25 cm length of gel squeezed from 15 gram tube". Formula: (l'w)/4=cm length Regranex. For a 1.5 cm'5 cm square wound: (1.5'1.5)/4=0.56 cm length Regranex®. As described in Regranex Package Insert, "the weight of Regranex gel from 15 g tube is 0.25 g/cm length". Regranex is 0.01% rhPDGF-BB or 100 μg/g Regranex. For 0.56 cm length of product, the weight of product is 0.14 g for a total dose of PDGF-BB of 14 μg. For sites treated with Regranex for 21 days, the maximum total dose for the study period (assuming no change in open wound size from Day 0) would be 14 μg/day'21 days or 294 μg of PDGFBB. However, at Days 7 and 14 the open wound size was determined for all Regranex treated sites, and the amount of Regranex applied was recalculated using the formula above ([1'w]/4=cm length Regranex).

b. Group3 rhPDGF and Group 2 Saline Dosages

The concentration of rhPDGF-BB used in the study was 0.3 mg/ml or 300 μg/ml. To not exceed a total dose for the study period of 294 μg PDGF-BB (same total maximum study dose as Regranex), a total of 0.98 ml of 0.3 mg/ml PDGF-BB would be applied to the wound site over the 21-day study period. Assuming a total of 3 administrations (days 0, 7, and 14), each administration would consist of >>327 μl PDGF-BB onto the collagen sponge representing a dose of approximately 98 μg PDGFBB/administration (slightly more than 7' the initial individual dose for Regranex treated sites). This represents a total of 145 μl per square centimeter of open wound surface area (327 μl/2.25 cm.sup.2 wound surface area).

The volume of 0.3 mg/ml PDGF-BB (Group 3) or buffer/sterile saline (Group 2) to be applied to the new collagen sponge on Days 7 and 14 was determined using the following formula:

145' cm² open wound surface area (length [cm]'width [cm] of open wound).

c. Collagen Sponge

As described above for Group 1 treated sites, all wounds were evaluated and measured at Days 7 and 14 to record the open wound measurements for each individual site. For sites treated with a collagen sponge (Group 2 and Group 3), the sponge was measured and trimmed to fit the open wound portion of the original wound following removal of the dressing, gentle rinsing of the site and documentation of findings, including measurements and photographic documentation.

C. Surgical Procedures

On Day 0, animals were anesthetized with isoflurane. The hair on the back was clipped and the skin swabbed with an aseptic solution. A template was used to mark a 1.5'1.5 cm square on the mid-back of the animal and a full thickness wound, corresponding to the template, was made by excising the skin and the panniculus *carnosus*. A hot water circulation pad or equivalent was placed under the animal to maintain normal body temperature during procedures, and animals recovered on a similar hot water circulation pad. Buprenorphine (0.06 mg/kg) was given by subcutaneous injections immediately after recovery from anesthesia and every 12 hours thereafter for 72 hours. Warmed Ringers solution (0.5 mL) was given by sub-cutaneous injection after the mice have recovered consciousness. The wounding of the animal was carried out under aseptic conditions. The wound site was photographed and the length and width measured immediately after excision and daily thereafter using a digital caliper. From Days 0 to 21, mice were administered test articles as listed in Table 1.

D. Study Results

1. Animal Survival

Three animals died or were prematurely euthanized during this study (all animals from Group 1: Regranex). The first animal was found dead one day after surgery (Animal #3). The second animal (Animal #1) had to be sacrificed on Day 5 due to self-mutilating the rear flank posterior to the wound site. Animal #5 in Group 1 had to be sacrificed on day 16 as a result of losing more than 20% of its starting body weight. The following Table 2 summarizes the animal deaths/sacrifice:

TABLE 2

Summary of Animal Deaths/Sacrifice

| Day 1 | Day 6 | Day 16 |
|---|---|---|
| Group 1, Animal #3 Found Dead | Group 1, Animal #1 Sacrificed, Self-Mutilating | Group 1, Animal #5 Exceeded 20% Weight Loss |

2. Wound Measurements

The wound area was measured using a digital caliper and the length (L) and width (W) of each wound was recorded. Wound area was calculated using the formula to calculate the area of a square, where A=L' W. Peak wound area was recorded on Day 0 for all three groups with subsequent decreases in mean wound area on Day 7. Day 14, and Day 21. All treated groups showed a substantial decrease in wound area during the course of the study.

To provide an additional measurement and account for wounds that may not of healed in the shape of a square (and therefore not be captured in the formula used above), the inside of the wounds were also measured by tracing the inside wound edge using ImageJ Software. The average wound area for all treatment groups by evaluation day (Day 0, Day 7, Day 14, and Day 21) was plotted as a scatter plot to provide a more detailed assessment of the individual measurements recorded on those days. For animals that died during the study, the last data point was carried forward. Positive results were achieved with fewer applications of the therapeutic composition. The amount of wound area reduction (mm$^2$) per cumulative number of treatments at each of the four time points (Day 0, Day 7, Day 14, and Day 21) for Groups 1 and 3 showed the average percent of wound closure over the course of the study for each Group. For animals that died, the last data point was carried forward.

3. Clinical Assessments

Wound images were also clinically assessed for possible differences in the degree of healing with respect to reepithelialization and formation of granulation tissue. Images of the wounds from each animal at each time point, Day 0, Day 7, Day 14, and Day 21, showed that Group 3 (rhPDGF/collagen sponge group) resulted in a demonstrable acceleration in the formation of granulation tissue and reepithelialization compared to Group 2 (the collagen sponge control group treated with buffer). In addition, wounds treated with Regranex daily (Group 1) also showed a better wound closure rate compared to Group 2 (the buffer control+collagen). Histopathology on formalin fixed samples of the wound areas was also performed and further corroborated accelerated wound healing resulting from treatment with the rhPDGF/collagen and Regranex treated wounds compared to buffer control treated sponges. The pathology also suggested even further improvement in reepithelialization in wounds treated with rhPDGF/collagen over Regranex treated. Representative samples of the histopathological samples are provided in FIGS. 13-18 of U.S. application Ser. No. 15/256,362, for example.

Regarding Group 1, the wound was 100% resurfaced at Day 21 (FIGS. 17 and 18), although some shearing was apparent due to the fragility of the dermal-epidermal architecture. 100% epidermal resurfacing was apparent, and the presence of differentiated stratification in the epidermis indicated its maturity. The neodermis still contained a high density of capillaries and new collagen formation was underway.

Regarding Group 2, the photomicrographs illustrated that a portion of the collagen sponge persisted in the wound bed for 21 days. In this wound edge the sponge appeared to obstruct the resurfacing of the epithelium (FIG. 13). Some granulation tissue developed beneath the collagen sponge. The collagen sponge appeared adherent in this region although infiltration with cells was minimal. A classic granulation tissue formed beneath the sponge.

Regarding Group 3, the wound was 100% resurfaced with epidermis (FIGS. 15 and 16). In the middle of the wound, all evidence of the original collagen sponge was gone. The wound was 100% resurfaced and was well-stratified with a stratum corneum indicating maturity. The neodermis showed evidence of new collagen production and the cellularity was decreased, indicating that the dermal tissue was maturing and losing the immature characteristics of granulation tissue.

E. Study Conclusions

The following conclusions were made from this study: (1) 21 applications of Regranex were given in Group 1, while only 3 applications of buffer/collagen or rhPDGF/collagen wound dressings were applied in Groups 2 and 3, respectively. (2) Three animals from Group 1 (Regranex) were either found dead or had to be euthanized during the in-life portion of the study. (3) All treated groups showed a decrease in wound area from Day 0-21 as determined by both caliper measurements and wound tracing using ImageJ® software analysis. At sacrifice (Day 21), 2 of 5 Regranex treated wounds, 3 of 5 rhPDGF/collagen treated wounds, and 0 of 5 collagen dressing treated wounds were healed (4) The raw images from each treatment showed that Group 3 (rhPDGF-BB/collagen) resulted in a demonstrable acceleration in the formation of granulation tissue and reepithelialization compared to the collagen wound dressing control group treated with buffer (Group 2). In addition, wounds treated with Regranex daily (Group 1) also showed a better closure rate compared to the control collagen sponge treated animals. (5) Healing assessed by wound reepithelialization was greatest in wounds treated with three applications of rhPDGF/collagen (Group 3) compared to 21 applications of Regranex (Group 1) or three applications of the collagen wound dressing wetted with saline. (6) Three weekly applications of rhPDGF/collagen (Group 3) accelerated wound closure, including granulation tissue formation and reepithelialization, compared to a collagen wound dressing (Group 2) and appeared at least as effective as 21 daily doses of Regranex Gel (Group 1). (7) rhPDGF/collagen was safe and effective, promoting better healing of diabetic wounds compared to the marketed collagen wound dressing. (8) rhPDGF-BB/collagen was safe and effective, promoting angiogenesis, granulation tissue formation, and reepithelialization compared to a marketed collagen wound dressing as demonstrated histologically. (9) rhPDGF/collagen, a sterile product, was highly biocompatible as demonstrated histologically. (10) rhPDGF/collagen was much easier to apply than Regranex Gel, which should improve patient compliance. (11) rhPDGF/collagen may be safer than Regranex, given that animals that received Regranex had a high mortality rate, while no such mortality was observed with rhPDGF/collagen or the collagen wound dressing.

Example 2 (Prophetic)

A study will be conducted to demonstrate the efficacy of the therapeutic compositions and wound treatment methods described herein in this study, three Study Groups are used to compare the effect of applying the therapeutic composition of the invention in a full-thickness skin tissue column (FTSTC) skin grafting model disclosed in C. L. Rettinger, J. L. Fletcher, A. H. Carlsson, R. K. Chan, "Accelerated epithelialization and improved wound healing metrics in porcine full-thickness wounds transplanted with full-thickness skin micrografts," *Wound Rep. Reg.* 25:816-827 (2017). In Group 1, the procedure of Rettinger et al. is used to apply FTSTC skin grafts to wounds in a pig model system. In Group 2, prior to treating the test animals with the FTSTCs, a sterile therapeutic composition comprising recombinant human platelet-derived growth factor BB homodimer (rhPDGF-BB) and a porous biocompatible carrier according to the present invention are applied to the surface of a skin wound. Group 3 is a control group that receives a sterile composition without rhPDGF-BB comprising only the porous biocompatible carrier, prior to treatment with FTSTCs. The study shows that Group 2, which receives the therapeutic composition comprising rhPDGF-BB, shows better wound healing than Groups 1 or 3. Group 2 shows demonstrable improvement in wound healing parameters in porcine fullthickness wounds, including acceleration in the formation of granulation tissue and reepithelialization, compared to the Groups that do not receive rhPDGF-BB.

A. Study Design

1. Animals

Female Yorkshire swine weighing 45-50 kg are utilized in this study. Animals are allowed to acclimatize for a minimum of 72 h upon arrival to the research facility, prior to initiation of any experimentation. Anesthesia and analgesia are administered and maintained by veterinary support staff from the research institute via standard protocols. Briefly, anesthesia is induced with an intramuscular injection of tiletamine-zolazepam (4-6 mg/kg) reinforced initially with 5% isoflurane administered through a facemask. General anesthesia is maintained with 1-30% isoflurane in 100 oxygen via endotracheal intubation. Buprenorphine HCL sustained release (0.12-0.24 mg/kg) is given subcutaneously 24 h prior to the surgical procedure and for 72 h as determined by postsurgical observations for pain management. Animals are sedated with Ketamine (10-25 mg/kg IM) and maintained under mask anesthesia for each assessment. Euthanasia is accomplished using intravenous injection of barbiturate given at 1.0 mL/10 lb of body weight at the end of the experiment. All procedures involving animals are approved by an appropriate institutional animal case board.

2. Harvesting Autologous Skin Micrografts

The skin around the dorsal neck region of the pig is depilated and thoroughly disinfected with successive applications of 10% povidone-iodine scrub and 70% isopropanol. FTSTCs with intact adnexa and subcutaneous tissue are obtained using a vacuum-assisted device developed and disclosed by. Rettinger et al. (see id.). This device utilizes commercially available biopsy punches (e.g., 1.5 mm in diameter) to core out full-thickness skin specimens mechanically by twisting and applying pressure to the donor skin. Harvested skin specimens are removed from the donor site and transported into a collected tube via air/fluid flows based on modifications of a mucus trap suction apparatus routinely used in the clinic. In Rettinger's system, the air flow is driven by a portable vacuum pump kept at a constant pressure. The closed fluid-flow loop within the device allows for transport and preservation of FTSTCs. Phosphate buffered saline (PBS) supplemented with antibiotics is used as the circulating fluid that keeps the specimens hydrated in the collection tube until ready for use. All components of the device (collection tube or silicone rubber tubing) are sterile 3. Porcine Skin Explant Culture Intact FTSTC's harvested using the vacuum-assisted device described above are used to initiate explant culture on fibrin gel-coated dishes in vitro. One milliliter of fibrinogen (10 mg/L) and thrombin (10 U/mL) mixture are added to tissue culture-treated culture dishes and allowed to solidify at 37° C. FTSTCs are evenly spread onto culture dishes treated with the fibrinogen/thrombin mixture. Minimal volume of cell culture media is added to the dish to promote adhesion of the explants, while keeping them hydrated. After 4-6 h of incubation, additional cell culture media is added to the dish. The cell culture media used in this in vitro study contains standard supplements, 10% fetal bovine serum, and antibiotics. Phase-contrast images of the skin explants and cells are obtained at different time points of culture using an inverted microscope. The viability and proliferative capability of skin explant-derived cells at different time points are assessed qualitatively using a standard viability/cytotoxicity assay kit and imaging analysis kit according to the manufacturers' recommendations. The explant-derived cells are also stained for basal keratinocyte marker cytokeratin 5, KS (Abcam, Cambridge, MA), following standard immunocytochemistry protocols, to demonstrate the presence of keratinocyte specific cell populations. KS-stained cells are visualized via confocal microscopy.

4. Wounding

Prior to wounding, the back of the anesthetized pig is shaved and depilated to remove any remaining hair. Preoperative markings of the wound edges are made using a permanent marker and then traced with an electric tattoo marker. The back of the pig is then thoroughly disinfected following standard protocols. Under general anesthesia and aseptic conditions, 40 full-thickness circular skin wounds measuring 3 cm in diameter and 2 cm apart are excised down to fascia using standard surgical techniques. Skin wounds are allowed to achieve hemostasis via electrocautery.

5. Treatment Regimens

In Group 1, the method disclosed in Rettinger et al. is used to treat the skin wounds with FTSTCs. FTSTCs are applied directly to excisional wounds at an expansion ratio of 1:16 in fibrin sealant. The experimental Groups are randomized to minimize any effects in healing rates that would depend on wound location Group 3 (control group) is broken down into sub-Groups (n=8) consisting of no FTSTC treatment and vehicle (fibrin gel only) controls. No particular attention is paid to the orientation or placement of the FTSTCs. FTSTCs are placed on their sides, equally spaced out on the wound bed. Each wound is covered with a Tegaderm® dressing, followed by gauze, Loban® tape and cloth jacket. The wounds are rebandaged with fresh dressing after each time point assessment until they are fully reepithelialized.

In Group 2, the method according to the present invention is used to pretreat the skin wounds, prior to the FTSTC treatment regimen used for Group 1 Group 3 (control group) is further broken down into a sub-Group (n=S) consisting of pretreatment with a sterile therapeutic composition comprising the porous biocompatible carrier according to the present invention but not containing rhPDGF-BB. The delivered rhPDGF-BB dosage, carrier composition, application regimen, and optional reapplication regimen is in accord with the embodiments disclosed above. In Group 2, the application of the sterile therapeutic composition delivers at least about 10 µg rhPDGF-BB per cm of wound surface area.

6. Histology

Full-thickness wound biopsies (3-5 mm wide strips) are excised across the wound bed to include unwounded skin and wound edge. Once biopsied, the wounds are excluded from further evaluation. Biopsies are collected at various time points (post-operative days, or PODs) postwounding (POD 1, 4, 7, 14, 21, 28, 60, 90). Samples are fixed in 10% neutral buffered formalin and processed for routine histological evaluation using an automatic tissue processor. Processed tissue specimens are embedded in paraffin blocks and stored at room temperature until use. 4.5 mm thick sections are cut from each sample and placed on treated glass slides, dried overnight in an oven set to 40° C., and then stored in room temperature until use.

Sections are deparaffinized and rehydrated in graded alcohols, stained with hematoxylin/cosin (H&E) using an autostainer, dehydrated, cleared, and mounted. Slides stained with H&E are imaged using a slide scanner and used for routine histological analysis and quantification. All quantification associated with these slides are assessed using standard image analysis software.

7. Immunohistochemistry

Immunohistochemistry is used to visualize cytokeratin 5 (basal keratinocytes), cytokeratin 10 (stratifying/differentiating keratinocytes), Ki67 for cell proliferation, alphas-mooth muscle actin (α-SMA) for myofibroblasts, and dermal vascularity (presence of pericytes). Briefly, tissue sections are de-paraffinized in xylene, rehydrated through graded alcohol washes, and incubated in 1' Antigen Retrieval Buffer/Citrate Buffer pH 6.0 (Abcam, Cambridge, MA) for 20 min in a vegetable steamer for heat-induced epitope retrieval. After several washes in 1' Tris-Buffered Saline with Tween 20 (TBST), tissue sections are blocked with 10% goat serum diluted in 1' TBST for 1 h in room temperature to minimize non-specific binding and incubated with each specific primary antibody overnight at 4° C. Fluor-conjugated secondary antibodies are used for immunofluorescence detection and are counterstained with DAP1. Negative controls are obtained by omitting incubation with the primary antibody. Primary antibodies used in this study are purchased from any standard supplier.

Fluorescent images of immunostained tissue sections were acquired using a slide scanner using exposure-matched settings. Furthermore, quantification of fluorescence intensity of αSMA immunohistochemistry is also performed using an image analysis software. Mean fluorescence intensity of cells expressing α-SMA in the wound is measured by applying a constant threshold across all of the data sets, followed by calculation of the sum of pixel intensities in a designated region of interest. Dermal vessels and epidermis are excluded from the analysis 8. Statistical Analysis All data are represented as mean value±standard deviation (SD). Data sets are examined for statistical significant using 1-way ANOVA with Tukey's multiple comparisons test for epithelial gap measurement or 2-war. ANOVA with Sidak's multiple comparisons test for αSMA quantification. A p-value of less or equal to 0.05 (p≤0.05) is considered significant.

B. Results

FTSTCs with a 1.5 mm diameter and length of 8 mm are consistently extracted from healthy donor skin. Each FTSTC consists of lull-thickness skin tissue, including epidermis and dermis, in addition to underlying hypodermis with intact adnexal (i.e., attached or adjunct) structures. The small wounds caused by extracting autologous skin tissue columns heals rapidly and completely reepithelialize within 4 days. Dermal and epidermal cells migrate readily out of undissociated FTSTC containing hypodermis. Cells grown from these skin explant specimens are a mixture of both dermal fibroblasts and epidermal keratinocytes. Viability and proliferative capability analyses of cells that have migrated out of the skin explants show few dead or compromised cells.

1. rhPDGF-BB Facilitation of Wound Reepithelialization and Reconstitution of Skin Adnexa Reepithelialization is assessed in rectangular biopsies (3-5 mm) taken across the entire wound bed at different time points post-transplantation. Histology of Group 1 animals shows that reepithelialization of the wounds grafted with FTSTCs is restored sooner than untreated and vehicle controls (Group 3). Cells from transplanted FTSTCs proliferate and migrate to the surface of the wounds about 10 days post-transplantation. Islands of newly formed epithelium are also evident upon macroscopic examination. By POD 14, wounds treated with FTSTCs are completely reepithelialized, whereas control wounds grafted without FTSTCs are not fully reepithelialized. Reepithelialization is further quantified via the epithelial gap measurement using H&E stained slides of the wound sections. The epithelial gap is defined as the distance between the advancing edges of keratinocyte migration measured in micrometers. FTSTC grafting results in a neo-epidermis that is more mature and differentiated than the control groups. Adnexal structures, such as hair follicles and sweat glands, are observed in FTSTC-treated wounds, but not the control groups. These adnexal structures are viable and well-integrated with the granulation tissue on POD) 14 They are more mature and resemble adnexal structures of normal skin by POD 60, whereas ungrafted wounds lack detectable skin adnexa.

In Group 2, which is pretreated with the therapeutic composition of the present invention, histology shows that reepithelialization of the wounds is restored sooner than wounds in Group 1, which are treated only with FTSTCs grafts. Controls show that the effect of the therapeutic composition is not due to the carrier. Compared to Group 1, wounds that are pretreated with rhPDGF-BB demonstrate faster proliferation and migration of cells from transplanted FTSTCs, faster maturation of a neo-epidermis, and enhanced maturation of adnexal structures.

Immunohistochemistry used to visualize α-SMA+myofibroblasts and pericytes from the vasculature shows significant differences between FTSTC-treated wounds or untreated controls (Group 1 versus Group 3) There is an abundance of α-SMA+ myofibroblasts in the granulation tissue of wounds treated with FTSTCs or untreated control wounds on POD 14; however, these myofibroblastic cells start to recede at an earlier time point by POD 28 in FTSTC-treated wounds and completely disappeared by POD 60. In contrast. α-SMA+myofibroblasts persist in the untreated controls until POD 60, and α-SMA is sometimes visible in small clusters at POD 90. In Group 2, the therapeutic composition (but not the carrier by itself) accelerates the recession of myofibroblastic cells from granulation tissue, thereby promoting the process of wound healing.

In terms of neovascularization, an abundance of immature vessels is observed in both FTSTC-treated wounds and untreated control. (Groups 1 and 3). No significant differences are found in the number of vessels from each group at POD 14 or POD 21. In Group 2, however, pretreatment with the therapeutic composition results in greater vessel maturation and reduction in the number of vessels, compared to Group 1 and 3 and controls using the therapeutic composition not containing rhPDGF-BB. The formation and maturation of granulation tissue in response to treatment with the therapeutic composition of the invention prior to the addition of the FTSTC thus facilitates wound repair.

Regarding cell proliferation, immunohistochemistry, is used to visualize Ki67+ cell populations in wounds. The Ki67 antigen is one of the most reliable markers for proliferating cells. Expression of Ki67 is detected during all active phases of the cell cycle ((G1, S, G2, M), but is absent in resting cells (G0). Rabbit polyclonal antibody against Ki67 is used to identify proliferative cells near or within transplanted FTSTCs or to assess cell proliferation in FTSTC grafted wounds over time. Transplanted FTSTCs proliferate and are incorporated into the newly formed granulation tissue. Application of rhPDGF-BB (Group 2), however, promotes the formation of granulation tissue prior to treatment with FTSTCs, enhancing the proliferation of cells from the FTSTC and wound healing The embodiments described herein do not provide all of the features and advantages set forth herein that may also be utilized, without departing from the spirit and scope of the present invention. Such modifications and variations are considered to be within the scope of the invention.

The invention claimed is:

1. A method of treating a skin wound, the method comprising:
   (1) treating the wound surface by applying a sterile therapeutic composition consisting essentially of recombinant human platelet-derived growth factor BB homodimer (rhPDGF-BB) optionally in a physiologic solution and a porous biocompatible carrier to the wound surface, wherein the porous biocompatible carrier is a collagen sponge or collagen wound dressing or a gelatin, and wherein the carrier provides a substrate for cell attachment and vascular ingrowth as the wound heals, and said applying delivers at least about 10 μg rhPDGF-BB per cm² of treated wound surface area up to 100 μg rhPDGF-BB per cm² treated wound surface area, optionally wherein prior to treating the wound surface the wound is debrided to remove necrotic or infected tissue;
   (2) optionally covering the wound with a dressing;
   (3) optionally using a treatment regimen of repeating steps (1) - (2) for 2 to 20 times at treatment intervals of three or more days; and
   (4) applying a skin-substitute composition to the treated wound and optionally covering the wound with a second dressing.

2. The method of claim 1, wherein steps (1) - (2) are repeated until granulation tissue covers the treated wound surface.

3. The method of claim 1, where the treatment regimen lasts no more than 7, 14, 21, 28, 35, 42, 50, 60, 70, 80, or 90 days.

4. The method of claim 1, wherein the treatment intervals are up to 7, 10, 14, or 21 days.

5. The method of claim 1, wherein the skin wound is a chronic ulcerated wound.

6. The method of claim 5, wherein the chronic ulcerated wound is selected from the group consisting of a venous ulcer (VU), venous leg ulcer (VLU), arterial/venous ulcer, arterial ulcer, diabetic foot ulcer (DFU), posttraumatic ulcer, and pressure ulcer.

7. The method of claim 1, wherein the skin wound is caused by thermal trauma.

8. The method of claim 1, wherein the skin wound is caused by surgery.

9. The method of claim 1, wherein the skin wound is partial thickness, full thickness, or deep wound.

10. The method of claim 1, wherein the wound surface area is greater than about 1 cm².

11. The method of claim 1, wherein the porous biocompatible carrier has a pore size distribution of between about 10 microns to about 2,000 microns.

12. The method of claim 1, wherein the porous biocompatible carrier has an average pore size of between about 50 microns to about 500 microns.

13. The method of claim 1, wherein the collagen sponge or collagen wound dressing comprises animal-sourced collagen.

14. The method of claim 1, wherein the collagen sponge or collagen wound dressing comprises at least 90% Type I collagen, at least 10% type Ill collagen, hydrolyzed collagen, monomeric collagen, or crosslinked collagen.

15. The method of claim 1, wherein the collagen sponge or collagen wound dressing comprises lyophilized collagen or gel-form collagen.

16. The method of claim 1, wherein the porous biocompatible carrier comprises an analgesic or antibiotic.

17. The method of claim 1, wherein the porous biocompatible carrier comprises an antiseptic.

18. The method of claim 1, wherein the wound dressing in step (1) or the dressing for covering the wound in steps (2) and (4) contains an analgesic or antibiotic.

19. The method of claim 1, wherein the wound dressing in step (1) or the dressing for covering the wound in steps (2) and (4) contains an antiseptic.

20. The method of claim 19, wherein the antiseptic is silver, polyhexarnethylene biguanide (PHMB), or polyhexadine.

21. The method of claim 1, wherein the skin-substitute composition comprises living cells.

22. The method of claim 21, wherein the living cells are stem cells.

23. The method of claim 22, wherein the stem cells are selected from the group consisting of mesenchymal stem cells, hematopoietic stem cells, epithelial stem cells, bone marrow stem cells, and adipose-derived stem cells.

24. The method of claim 22, wherein the stem cells are at a dose of about 1,500 to about 30,000, or about 2,000 to about 25,000, or about 2,500 to about 20,000 stem cells per square centimeter of would surface.

25. The method of claim 22, wherein the overall dosage of the stem cells per treatment is about 1 million to about 10 million, or about 3 million to about 8 million, or about 4 million to about 6 million stem cells.

26. The method of claim 22 wherein the method further comprises injecting into or around the wound at least one additional dose of stem cells to treat the wound at least 7 days or at least 14 days or at least 21 days following the initial treatment.

27. The method of claim 21, wherein the living cells comprise one or more of epithelial cells, endothelial cells, keratinocytes, fibroblasts, adipose-derived stromal vascular fraction (SVF) cells, and platelets.

28. The method of claim 27, wherein the living cells comprise epithelial cells.

29. The method of claim 21, wherein the living cells comprise cultured cells.

30. The method of claim 1, wherein the skin-substitute composition comprises mesenchymal stem cells, epithelial cells, or keratinocytes.

31. The method of claim 1, wherein said skin-substitute composition comprises a biodegradable synthetic component.

32. The method of claim 1, wherein the skin-substitute composition comprises an autologous, allogenic, or xenogenic skin graft.

33. The method of claim 32, wherein the autologous, allogenic, or xenogenic skin graft is a split-thickness skin graft (STSG).

34. The method of claim 32, wherein the autologous, allogenic, or xenogenic skin graft is a full-thickness skin graft (FTSG) or a full-thickness skin tissue column (FTSTC).

35. The method of claim 1, wherein the skin-substitute composition is applied topically to the wound surface by placing or injecting the skin-substitute composition onto the wound surface.

36. The method of claim 2, wherein the skin-substitute composition is applied over the granulation tissue covering the treated wound surface.

37. The method of claim 1, wherein said skin-substitute composition provides a permanent, semi-permanent, or temporary cover for the skin wound.

38. The method of claim 1, wherein the sterile therapeutic composition is free from an enzyme inhibitor.

* * * * *